(12) United States Patent
Roth et al.

(10) Patent No.: US 12,318,505 B2
(45) Date of Patent: Jun. 3, 2025

(54) ORTHOPEDIC MEDICAL DEVICES THAT INCLUDE COATING MATERIAL

(71) Applicant: MiRus LLC, Marietta, GA (US)

(72) Inventors: Noah Roth, Marietta, GA (US); Jay Yadav, Atlanta, GA (US); Jordan Bauman, Smyrna, GA (US)

(73) Assignee: MIRUS LLC, Marietta, GA (US)

( * ) Notice: Subject to any disclaimer, the term of this patent is extended or adjusted under 35 U.S.C. 154(b) by 0 days.

(21) Appl. No.: 18/422,748

(22) Filed: Jan. 25, 2024

(65) Prior Publication Data

US 2024/0197957 A1      Jun. 20, 2024

Related U.S. Application Data

(63) Continuation-in-part of application No. 18/417,939, filed on Jan. 19, 2024, and a continuation-in-part of application No. 18/418,007, filed on Jan. 19, 2024, and a continuation-in-part of application No. 18/204,180, filed on May 31, 2023.

(60) Provisional application No. 63/540,266, filed on Sep. 25, 2023, provisional application No. 63/537,585, filed on Sep. 11, 2023, provisional application No. (Continued)

(51) Int. Cl.
| | | |
|---|---|---|
| A61L 27/30 | (2006.01) | |
| A61L 27/04 | (2006.01) | |
| A61L 27/54 | (2006.01) | |
| A61L 31/02 | (2006.01) | |
| A61L 31/08 | (2006.01) | |
| A61L 31/16 | (2006.01) | |

(52) U.S. Cl.
CPC .............. *A61L 27/306* (2013.01); *A61L 27/04* (2013.01); *A61L 27/54* (2013.01); *A61L 31/022* (2013.01); *A61L 31/088* (2013.01); *A61L 31/16* (2013.01); *A61L 2300/114* (2013.01); *A61L 2420/08* (2013.01)

(58) Field of Classification Search
CPC ........ A61L 27/306; A61L 27/04; A61L 27/54; A61L 31/022; A61L 31/088; A61L 31/16; A61L 2300/114; A61L 2420/08
See application file for complete search history.

(56) References Cited

U.S. PATENT DOCUMENTS 10,729,813 B2 *  8/2020  Badylak ................... A61L 27/38
11,266,767 B2   3/2022  Roth et al.
(Continued)

FOREIGN PATENT DOCUMENTS

WO      2017132729       8/2017

OTHER PUBLICATIONS

Pedowitz et al., "Molybdenum Rhenium (MoRe) as a Biologically superior Alloy for Foot and Ankle Implants" Foot & Ankle Orthopaedics, vol. 3, p. 1 (Sep. 2018).
(Continued)

*Primary Examiner* — Jerrah Edwards
*Assistant Examiner* — Aren Patel
(74) *Attorney, Agent, or Firm* — UB Greensfelder LLC; Brian E. Turung

(57) ABSTRACT

An orthopedic medical device that is at least partially coated with an enhancement coating, and a method for inserting the orthopedic medical device in a patient. One type of enhancement coating that can be used includes titanium oxynitride or titanium nitride oxide (TiNOx) and/or zirconium oxynitride (ZrNxOy).

30 Claims, 1 Drawing Sheet

Related U.S. Application Data

63/439,892, filed on Jan. 19, 2023, provisional application No. 63/439,908, filed on Jan. 19, 2023, provisional application No. 63/389,281, filed on Jul. 14, 2022, provisional application No. 63/347,337, filed on May 31, 2022.

(56) References Cited

U.S. PATENT DOCUMENTS

| | | |
|---|---|---|
| 2003/0072974 A1 | 4/2003 | Lau et al. |
| 2003/0159920 A1 | 8/2003 | Roth |
| 2005/0079200 A1 | 4/2005 | Rathenow et al. |
| 2005/0191408 A1 | 9/2005 | Aharonov |
| 2006/0200224 A1 | 2/2006 | Furst et al. |
| 2006/0136051 A1 | 6/2006 | Furst et al. |
| 2006/0184251 A1 | 8/2006 | Zhang et al. |
| 2008/0183280 A1 | 7/2008 | Agnew |
| 2009/0068249 A1 | 3/2009 | Furst et al. |
| 2010/0023115 A1 | 1/2010 | Robain et al. |
| 2013/0084322 A1 | 4/2013 | Wu |
| 2013/0216421 A1 | 8/2013 | Buckman, Jr. et al. |
| 2014/0099279 A1 | 4/2014 | Furst et al. |
| 2015/0282929 A1 | 10/2015 | Rodriguez |
| 2016/0237541 A1* | 8/2016 | Patel .................. B21C 23/002 |
| 2016/0339144 A1* | 11/2016 | McEntire ............ A61L 27/446 |
| 2017/0216494 A1 | 8/2017 | Roth et al. |
| 2017/0273785 A1 | 9/2017 | Seguin et al. |
| 2018/0361017 A1 | 12/2018 | Roth |
| 2019/0008995 A1 | 1/2019 | Roth |
| 2019/0046684 A1 | 2/2019 | Roth et al. |
| 2020/0254140 A1* | 8/2020 | Roth .................... A61L 27/042 |
| 2020/0306067 A1 | 10/2020 | Nia |
| 2021/0038379 A1 | 2/2021 | Johnson et al. |
| 2021/0251766 A1* | 8/2021 | Quintana-Ponce ..... A61F 2/389 |
| 2022/0192841 A1* | 6/2022 | Blain ..................... A61F 2/447 |
| 2023/0270680 A1* | 8/2023 | Fritz .................... A61K 33/24 |
| | | 424/489 |

OTHER PUBLICATIONS

Alotaibi et al., "Antibacterial Properties of Cu-Zr02 Thin Film Prepared via Aerosol Assisted Chemical Vapour Deposition", Journal of Materials Chemistry B, pp. 1-15 (2015).

Singh et al., "Synthesis of New Zirconium (IV) Complexes with Amino Acid Schiff Bases: Spectral, Molecular Modeling, and Fluoresence Studies"; International Journal of Inorganic Chemistry, pp. 5-6 (Jan. 2013).

Kumari et al., "Zirconia-based nanomaterials: recent developments in syntheses and applications" Nanoscale Advances, vol. 4, pp. 4210-4236 (2022).

* cited by examiner

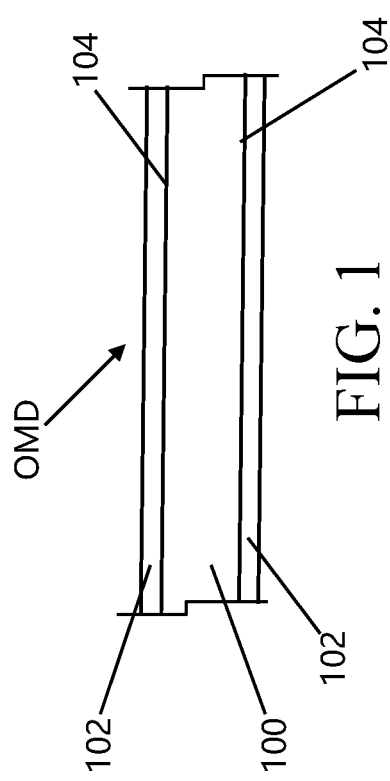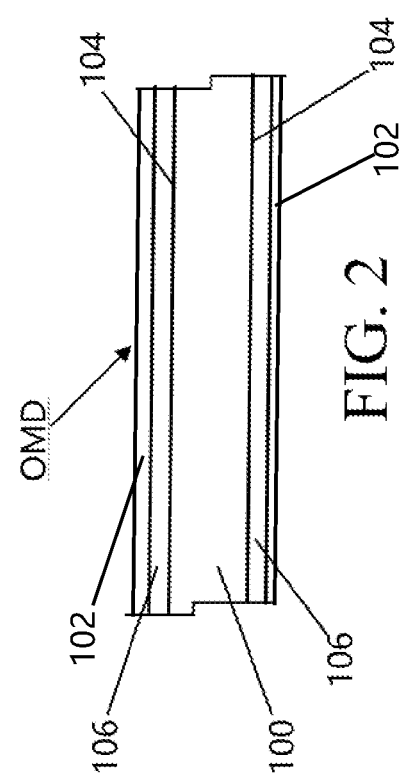

ORTHOPEDIC MEDICAL DEVICES THAT INCLUDE COATING MATERIAL

REFERENCED APPLICATIONS

The present application claims priority to U.S. Provisional Application Ser. No. 63/540,266 filed Sep. 25, 2023, which is all fully incorporated herein by reference.

The present application claims priority to U.S. Provisional Application Ser. No. 63/537,585 filed Sep. 11, 2023, which is incorporated herein by reference.

The present disclosure is a continuation-in-part of U.S. application Ser. No. 18/417,939 filed Jan. 19, 2024, which in turn claims priority on U.S. Provisional Application Ser. No. 63/439,892, filed Jan. 19, 2023, which are all fully incorporated herein by reference.

The present disclosure is a continuation-in-part of U.S. application Ser. No. 18/418,007 filed Jan. 19, 2024, which in turn claims priority on U.S. Provisional Application Ser. No. 63/439,908, filed Jan. 19, 2023, which are all fully incorporated herein by reference.

The present application is a continuation-in-part of U.S. application Ser. No. 18/204,180 filed May 31, 2023, which claims priority on U.S. Provisional Application Ser. No. 63/389,281 filed Jul. 14, 2022, which are all fully incorporated herein by reference.

The present application is a continuation-in-part of U.S. application Ser. No. 18/204,180 filed May 31, 2023, which claims priority on U.S. Provisional Application Ser. No. 63/347,337 filed May 31, 2022, which are all fully incorporated herein by reference.

FIELD OF DISCLOSURE

The disclosure relates medical devices that are coated with coatings, particularly to medical devices that are partially or fully coated with a coating that improves the success rate of the implanted medical device, more particularly to orthopedic medical devices that are partially or fully that coated with a coating that improves the success rate of the implanted orthopedic medical device, and still particularly to orthopedic medical devices that are partially or fully formed of a metal alloy and the metal alloy is coated with a titanium oxynitride and/or a zirconium oxynitride coating that can improve the success rate of the implanted orthopedic medical device.

BACKGROUND OF DISCLOSURE

Stainless steel, cobalt-chromium alloys, TiNi alloys, and TiAlV alloys are some of the more common metal alloys used for various types of medical devices. Although these alloys have been successful in forming a variety of medical devices, these alloys have several deficiencies.

When a medical device is inserted into a patient, it is typically desirable for the medical device to resist ionization and/or corrosion while in the patient so as to not subject the patient to metal ions and/or oxides from the metals used to form the medical device while in the patient. Excessive ion release from the medical device can potentially be adverse to the patient. Although tradition materials such as stainless steel (316L), cobalt-chromium alloys (e.g., MP35N, etc.), Nitinol, TiAlV alloys are relatively stable when inserted into patients, some degree of metal ion release occurs when the medical device is located in the patient. However, many of the common metal alloys used for implantable medical devices include chromium and/or nickel; two elements that can cause adverse reactions in some patients. For example, nickel and/or cobalt ion release from metal alloys that includes one or both of such metals can result in allergic reaction with surrounding tissue that can in turn result in the failure of the implant. However, prior art metal alloys that are absent both nickel and cobalt are typically too brittle for use in many orthopedic applications.

In view of the current state of the art of orthopedic medical devices, there is a need for an improved orthopedic medical device that a) has reduced nickel and chromium metal content and/or has reduced ion release as compared to orthopedic medical devices that are partially or fully formed of stainless steel alloy, cobalt-chromium alloy, and TiNi alloy so as to reduce or eliminate problems associated with allergic reactions with surrounding tissue that can be at least partially caused by chromium and/or nickel, b) is partially or fully formed of a metal alloy that has improve strength, surface hardness, and/or ductility as compared to stainless steel alloy, cobalt-chromium alloy, TiNi alloy, and TiAlV alloy, c) promotes the formation and/or release of nitric oxide (NO) from the implanted orthopedic medical device so as to improve the success rate of the implanted orthopedic medical device, d) promotes bone healing about the implanted orthopedic medical device, and/or e) reduces bacterial growth and/or bacterial infection about the implanted orthopedic medical device.

SUMMARY OF THE DISCLOSURE

The present disclosure is direct to an orthopedic medical device that is coated with a material, and wherein the coated orthopedic medical device has improved success rates after implantation. The orthopedic medical device has one or more properties and/or features, namely a) is formed of a material that is fully absent nickel and/or chromium content or has reduced amounts of nickel and/or chromium as compared to orthopedic medical devices that are partially or fully formed of stainless steel alloy, cobalt-chromium alloy, and TiNi alloy so as to reduce or eliminate problems associated with allergic reactions with surrounding tissue that can be at least partially caused by chromium and/or nickel, b) has reduced ion release of nickel and/or chromium so as to reduce or eliminate problems associated with allergic reactions with surrounding tissue that can be at least partially caused by chromium and/or nickel, c) has an outer surface that is absent nickel and/or chromium and/or has reduced amounts of nickel and/or chromium as compared to orthopedic medical devices that are partially or fully formed of stainless steel alloy, cobalt-chromium alloy, and TiNi alloy so as to reduce or eliminate problems associated with allergic reactions with surrounding tissue that can be at least partially caused by chromium and/or nickel, d) is partially or fully formed of a metal alloy that has increased strength, increased surface hardness, and/or increased ductility as compared to stainless steel alloy, cobalt-chromium alloy, TiNi alloy, and TiAlV alloy, e) has an outer surface that promotes the formation and/or release of nitric oxide (NO) from the implanted orthopedic medical device so as to improve the success rate of the implanted orthopedic medical device, f) has an outer surface that promotes bone healing about the implanted orthopedic medical device, g) has an outer surface that reduces bacterial growth and/or bacterial infection about the implanted orthopedic medical device, and/or h) has an outer surface that improves the biocompatibility of the implanted orthopedic medical device.

In one non-limiting aspect of the disclosure, the orthopedic medical device is in the form of a spinal implant; frame and other structure for use with a spinal implant; bone implant; artificial disk; artificial spinal disk; spinal interbody; expandable spinal interbody; interbody fusion device; expandable interbody fusion device; prosthetic implant or device to repair, replace and/or support a bone (e.g., acromion, atlas, axis, calcaneus, carpus, clavicle, coccyx, epicondyle, epitrochlea, femur, fibula, frontal bone, greater trochanter, humerus, ilium, ischium, mandible, maxilla, metacarpus, metatarsus, occipital bone, olecranon, parietal bone, patella, phalanx, radius, ribs, sacrum, scapula, sternum, talus, tarsus, temporal bone, tibia, ulna, zygomatic bone, etc.) and/or cartilage; bone plate nail; spinal rod; bone screw; post; spinal cage; bone plate; pedicle screw; cap; hinge; joint system; anchor; spacer; shaft; anchor; disk; ball; tension band; locking connector or other structural assembly that is used in a body to support a structure, mount a structure, and/or repair a structure in a body such as, but not limited to, a human body, animal body, etc. In one non-limiting embodiment, the orthopedic medical device is a spinal rod; pedicle screw; bone plate; artificial spinal disk; artificial spinal disk; spinal interbody; expandable spinal interbody; interbody fusion device; expandable interbody fusion device; or prosthetic implant or device to repair, replace and/or support a bone.

In another non-limiting aspect of the present disclosure, the outer surface of the orthopedic medical device is at least partially (e.g. 1-99.999 wt. % and all values and ranges therebetween) or fully formed of a material that is coated with an enhancement coating used to a) reduced metal ion release of the metal material from the orthopedic medical device, b) reduce the rate of corrosion on the metal that forms the orthopedic medical device, c) form an outer surface of the orthopedic medical device that is absent nickel and/or chromium, d) increased a surface hardness of the orthopedic medical device, e) promote the formation and/or release of nitric oxide (NO) from the implanted orthopedic medical device, f) promote bone healing about the orthopedic medical device, g) inhibit or reduce neointimal hyperplasia/cell overgrowth onto one or more portions of the orthopedic medical device after implantation in the treatment area, h) reduce infection about the orthopedic medical device after implantation in the treatment area, i) reduce bacterial growth and/or bacterial infection about the implanted orthopedic medical device, j) improve the biocompatibility of the implanted orthopedic medical device, k) reduce the incidence of nickel exposure and/or ion release from the orthopedic medical device that can react with cells about the orthopedic medical device after implantation in the treatment area, l) reduce inflammatory cell response about the orthopedic medical device after implantation in the treatment area. In another non-limiting embodiment, the enhancement coating on one or more portions of the orthopedic medical device is formulated to provide and/or promote generation of nitric oxide near, at and/or in adjacent tissue. Nitric oxide can reduce neointimal hyperplasia, reduce tissue proliferation, all of which can contribute to an improved pro-healing environment. In another non-limiting embodiment, the enhancement coating provides, promotes and/or facilitates in a) formation or generation of nitric oxide (NO), b) stimulation of cells about the implanted orthopedic medical device, and/or c) enhance modulation of cells about the implanted orthopedic medical device. In one non-limiting arrangement, the enhancement coating is a metal oxynitride layer that is deposited a portion (e.g., 1-99.990% of the outer surface and all values and ranges therebetween) or all of outer surface of the orthopedic medical device. In one non-limiting specific configuration, the metal oxynitride layer is or includes titanium oxynitride and/or zirconium oxynitride. In another non-limiting specific configuration, thickness of the metal oxynitride layer is 10 nanometers to 10 microns (and all values and ranges therebetween). In one non-limiting specific configuration, the oxygen to nitrogen atomic ratios of the metal oxynitride layer is 1:10 to 10:1 (and all values and ranges therebetween). In another non-limiting specific configuration, the coating of metal oxynitride layer is optionally deposited onto a metallic adhesion layer in between the base substrate of the orthopedic medical device and the oxynitride layer. In another non-limiting specific configuration, the adhesion layer, when used, optionally is or includes titanium metal and/or zirconium metal. The thickness of the adhesion layer optionally has a thickness of at least 10 nanometers (e.g., 10 to 500 nanometers and all values and ranges therebetween). When the metal oxynitride layer is deposited on a portion or all of the outer surface of the orthopedic medical device, the metal oxynitride coating can be used to enhance healing about the orthopedic medical device and/or to increase the operational life of the orthopedic medical device.

Nitric oxide (NO) is a short-lived, gaseous, signal molecule responsible for a plurality of cellular functions throughout the human body. NO is endogenously biosynthesized from L-arginine, oxygen, and NADPH inputs via the Nitric Oxide Synthase enzyme family. In the body, NO acts as a potent vasodilator. NO is also involved in cellular repair. A primary effect of NO is binding to Soluble Guanylyl Cyclase (sGC) activating synthesis of a downstream signaling molecule Cyclic Guanosine Monophosphate (cGMP). cGMP is subsequently responsible for downregulation of factors responsible for platelet aggregation, apoptosis, inflammation, and tissue remodeling. cGMP is also responsible for upregulation of factors responsible for vasodilation. Examples of direct nitric oxide donors includes agents with nitroso or nitrosyl functional groups that spontaneously release nitric oxide. Examples of metabolic nitric oxide donors include agents with organic nitrate and nitrite esters requiring enzymatic metabolism to generate bioactive nitric oxide. Examples of bifunctional nitric oxide donors include agents with nitrate esters and S-nitrosothiols that release nitric oxide simultaneously with performing additional pharmacological benefits.

In accordance with another and/or alternative non-limiting aspect of the present disclosure, the orthopedic medical device is partially (e.g., 1-99.999 wt. % and all values and ranges therebetween) or fully formed of a metal material that includes a) stainless steel, b) CoCr alloy or MP35N alloy or a Phynox alloy or Elgiloy alloy or L605 alloy, c) TiAlV alloy, d) aluminum alloy, e) nickel alloy, f) titanium alloy, g) tungsten alloy, h) molybdenum alloy, i) copper alloy, j) beryllium-copper alloy, k) Nitinol alloy, l) refractory metal alloy, or m) metal alloy that includes at least 5 atomic weight percent (awt. %) or atomic percentage (awt. %) rhenium (e.g., 5-99 awt. % rhenium and all values and ranges therebetween). As used herein, atomic weight percent (awt. %) or atomic percentage (awt. %) or atomic percent (awt. %) are used interchangeably. As defined herein, the weight percentage (wt. %) of an element is the weight of that element measured in the sample divided by the weight of all elements in the sample multiplied by 100. The atomic percentage or atomic weight percent (awt. %) is the number of atoms of that element, at that weight percentage, divided by the total number of atoms in the sample multiplied by 100. The use of the terms weight percentage (wt. %) and atomic percentage or atomic weight percentage (awt. %) are two ways of referring to metallic alloy and its constituents. It has been found that for several metal alloys the inclusion of at least 15 awt. % rhenium results in the ductility and/or tensile strength of the metal alloy to improve as compared to a metal alloy is that absent rhenium. Such improvement in ductility and/or tensile strength due to the inclusion of at least 15 awt. % rhenium in the metal alloy is referred to as the "rhenium effect." As defined herein, a "rhenium effect" is a) an increase of at least 10% in ductility of the metal alloy caused by the addition of rhenium to the metal alloy, and/or b) an increase of at least 10% in tensile strength of the metal alloy caused by the addition of rhenium to the metal alloy. As defined herein, a refractory metal alloy is a metal alloy that includes at least 20 wt. % of one or more of molybdenum, rhenium, niobium, tantalum or tungsten. Non-limiting refractory metal alloys include MoRe alloy, ReW alloy, MoReCr alloy, MoReTa alloy, MoReTi alloy, WCu alloy, ReCr, molybdenum alloy, rhenium alloy, tungsten alloy, tantalum alloy, niobium alloy, etc. In one non-limiting arrangement, 50-100 wt. % (and all values and ranges therebetween) of the orthopedic medical device is formed of a refractory metal alloy or a metal alloy that includes at least 15 awt. % rhenium. In another non-limiting arrangement, the metal alloy that is used to partially or fully form the orthopedic medical device includes at least 30 wt. % (e.g., 30-99 wt. % and all values and ranges therebetween) of one or more of molybdenum, rhenium, niobium, tantalum or tungsten. In another non-limiting embodiment, the refractory metal alloy or the metal alloy that includes at least 15 awt. % rhenium can be used to 1) increase the radiopacity of the orthopedic medical device, 2) increase the radial strength of the orthopedic medical device, 3) increase the yield strength and/or ultimate tensile strength of the orthopedic medical device, 4) improve the stress-strain properties of the orthopedic medical device, 5) improve the bendability and/or flexibility of the orthopedic medical device, 6) improve the strength and/or durability of the orthopedic medical device, 7) increase the hardness of the orthopedic medical device, 8) improve the biostability and/or biocompatibility properties of the orthopedic medical device, 9) increase fatigue resistance of the orthopedic medical device, 10) resist cracking in the orthopedic medical device, 11) resist propagation of cracks in the orthopedic medical device, 12) enable smaller, thinner, and/or lighter weight orthopedic medical devices to be made, 13) reduce adverse tissue reactions with the orthopedic medical device, 14) reduce metal ion release from the orthopedic medical device after implantation of the orthopedic medical device, 15) reduce corrosion of the orthopedic medical device after implantation of the orthopedic medical device, 16) reduce allergic reaction with the orthopedic medical device after implantation of the orthopedic medical device, 17) improve hydrophilicity of the orthopedic medical device, 18) reduce magnetic susceptibility of the orthopedic medical device, and/or 18) reduce toxicity of the orthopedic medical device after implantation of the orthopedic medical device.

In another and/or alternative non-limiting aspect of the disclosure, the orthopedic medical device is optionally partially or fully formed of stainless steel, CoCr alloys, TiAlV alloys, aluminum alloys, nickel alloys, titanium alloys, tungsten alloys, molybdenum alloys, copper alloys, MP35N alloys, beryllium-copper alloys that have been modified to include at least 15 awt. % rhenium so as to result in improved ductility and/or tensile strength as compared to the same metal alloy that is absent rhenium. As defined herein, a stainless-steel alloy (SS alloy) includes at least 50 wt. % (weight percent) iron, 10-28 wt. % chromium, 0-35 wt. % nickel, and optionally one or more of 0-4 wt. % molybdenum, 0-2 wt. % manganese, 0-0.75 wt. % silicon, 0-0.3 wt. % carbon, 0-5 wt. % titanium, 0-10 wt. % niobium, 0-5 wt. % copper, 0-4 wt. % aluminum, 0-10 wt. % tantalum, 0-1 wt. % Se, 0-2 wt. % vanadium, and 0-2 wt. % tungsten. A 316L alloy that falls within a stainless-steel alloy includes 17-19 wt. % chromium, 13-15 wt. % nickel, 2-4 wt. % molybdenum, 2 wt. % max manganese, 0.75 wt. % max silicon, 0.03 wt. % max carbon, balance iron. As defined herein, a cobalt-chromium alloy (CoCr alloy) includes 30-68 wt. % cobalt, 15-32 wt. % chromium, and optionally one or more of 1-38 wt. % nickel, 2-18 wt. % molybdenum, 0-18 wt. % iron, 0-1 wt. % titanium, 0-0.15 wt. % manganese, 0-0.15 wt. % silver, 0-0.25 wt. % carbon, 0-16 wt. % tungsten, 0-2 wt. % silicon, 0-2 wt. % aluminum, 0-1 wt. % iron, 0-0.1 wt. % boron, 0-0.15 wt. % silver, and 0-2 wt. % titanium. As a MP35N alloy that falls within a CoCr alloy includes 18-22 wt. % chromium, 32-38 wt. % nickel, 8-12 wt. % molybdenum, 0-2 wt. % iron, 0-0.5 wt. % silicon, 0-0.5 wt. % manganese, 0-0.2 wt. % carbon, 0-2 wt. % titanium, 0-0.1 wt. %, 0-0.1 wt. % boron, 0-0.15 wt. % silver, and balance cobalt. As defined herein, a Phynox and Elgiloy alloy that falls within a CoCr alloy includes 38-42 wt. % cobalt, 18-22 wt. % chromium, 14-18 wt. % iron, 13-17 wt. % nickel, 6-8 wt. % molybdenum. As defined herein, a L605 alloy that falls within a CoCr alloy includes 18-22 wt. % chromium, 14-16 wt. % tungsten, 9-11 wt. % nickel, balance cobalt. As defined herein, a titanium-aluminum-vanadium alloy (TiAlV alloy) includes 4-8 wt. % aluminum, 3-6 wt. % vanadium, 80-93 wt. % titanium, and optionally one or more of 0-0.4 wt. % iron, 0-0.2 wt. % carbon, 0-0.5 wt. % yttrium. A Ti-6Al-4V alloy that falls with a TiAlV alloy includes incudes 3.5-4.5 wt. % vanadium, 5.5-6.75 wt. % aluminum, 0.3 wt. % max iron, 0.08 wt. % max carbon, 0.05 wt. % max yttrium, balance titanium. As defined herein, an aluminum alloy includes 80-99 wt. % aluminum, and optionally one or more 0-12 wt. % silicon, 0-5 wt. % magnesium, 0-1 wt. % manganese, 0-0.5 wt. % scandium, 0-0.5 wt. % beryllium, 0-0.5 wt. % yttrium, 0-0.5 wt. % cerium, 0-0.5 wt. % chromium, 0-3 wt. % iron, 0-0.5, 0-9 wt. % zinc, 0-0.5 wt. % titanium, 0-3 wt. % lithium, 0-0.5 wt. % silver, 0-0.5 wt. % calcium, 0-0.5 wt. % zirconium, 0-1 wt. % lead, 0-0.5 wt. % cadmium, 0-0.05 wt. % bismuth, 0-1 wt. % nickel, 0-0.2 wt. % vanadium, 0-0.1 wt. % gallium, and 0-7 wt. % copper. As defined herein, a nickel alloy includes 30-98 wt. % nickel, and optionally one or more 5-25 wt. % chromium, 0-65 wt. % iron, 0-30 wt. % molybdenum, 0-32 wt. % copper, 0-32 wt. % cobalt, 2-2 wt. % aluminum, 0-6 wt. % tantalum, 0-15 wt. % tungsten, 0-5 wt. % titanium, 0-6 wt. % niobium, 0-3 wt. % silicon. As defined herein, a titanium alloy includes 80-99 wt. % titanium, and optionally one of more of 0-6 wt. % aluminum, 0-3 wt. % tin, 0-1 wt. % palladium, 0-8 wt. % vanadium, 0-15 wt. % molybdenum, 0-1 wt. % nickel, 0-0.3 wt. % ruthenium, 0-6 wt. % chromium, 0-4 wt. % zirconium, 0-4 wt. % niobium, 0-1 wt. % silicon, 0.0.5 wt. % cobalt, 0-2 wt. % iron. As defined herein, a tungsten alloy includes 85-98 wt. % tungsten, and optionally one or more of 0-8 wt. % nickel, 0-5 wt. % copper, 0-5 wt. % molybdenum, 0-4 wt. % iron. As defined herein, a molybdenum alloy includes 90-99.5 wt. % molybdenum, and optionally one or more of 0-1 wt. % nickel, 0-1 wt. % titanium, 0-1 wt. % zirconium, 0-30 wt. % tungsten, 0-2 wt. % hafnium, 0-2 wt. % lanthanum. As defined herein, a copper alloy includes 55-95 wt. % copper, and optionally one or more of 0-40 wt. % zinc, 0-10 wt. % tin, 0-10 wt. % lead, 0-1 wt. % iron, 0-5 wt. % silicon, 0-12 wt. % manganese, 0-12 wt. % aluminum, 0-3 wt. % beryllium, 0-1 wt. % cobalt, 0-20 wt. % nickel. As defined herein, a beryllium-copper alloy includes 95-98.5 wt. % copper, 1-4 wt. % beryllium, and optionally one or more of 0-1 wt. % cobalt, and 0-0.5 wt. % silicon. As defined herein, a titanium-nickel alloy (e.g., Nitinol alloy) includes 42-58 wt. % nickel and 42-58 wt. % titanium.

In accordance with another and/or alternative non-limiting aspect of the present disclosure, the orthopedic medical device is partially or fully formed of a metal material that includes a metal alloy that contains at least 15 awt. % rhenium. It has been found for some metal alloys (e.g., stainless steel, CoCr alloys, TiAlV alloys, aluminum alloys, nickel alloys, titanium alloys, tungsten alloys, molybdenum alloys, copper alloys, MP35N alloys, beryllium-copper alloys, etc.), the inclusion of at least 15 awt. % rhenium results in improved ductility and/or tensile strength. It has been found that the addition of rhenium to a metal alloy can result in the formation of a twining alloy in the metal alloy that results in the overall ductility of the metal alloy to increase as the yield and tensile strength increases as a result of reduction and/or work hardening of the metal alloy that includes the rhenium addition. The rhenium effect has been found to occur when the atomic weight of rhenium in the metal alloy is at least 15 awt. % (e.g., 15-99 awt. % rhenium in the metal alloy and all values and ranges therebetween). For example, for stainless-steel alloys, the rhenium effect can begin to be present when the stainless-steel alloy is modified to include a rhenium amount of at least 5-10 wt. % (and all values and ranges therebetween) of the stainless-steel alloy. For CoCr alloys, the rhenium effect can begin to be present when the CoCr alloy is modified to include a rhenium amount of at least 4.8-9.5 wt. % (and all values and ranges therebetween) of the CoCr alloy. For TiAlV alloys, the rhenium effect can begin to be present when the TiAlV alloy is modified to include a rhenium amount of at least 4.5-9 wt. % (and all values and ranges therebetween) of the TiAlV alloy. It can be appreciated, the rhenium content in the above non-limiting examples can be greater than the minimum amount to create the rhenium effect in the metal alloy.

In accordance with another and/or alternative aspect of the present disclosure, the metal alloy that is used to partially or fully form the orthopedic medical device includes at least 5 awt. % (e.g., 5-99 awt. % and all values and ranges therebetween) rhenium, and at least 0.1 wt. % (e.g., 0.1 wt. % to 96 wt. % and all values and ranges therebetween) of one or more additives selected from the group of aluminum, boron, beryllium, bismuth, cadmium, calcium, cerium, chromium, cobalt, copper, gallium, gold, hafnium, iridium, iron, lanthanum, lanthanum oxide, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other components other than the additives (e.g., carbon, oxygen, phosphorous, sulfur, hydrogen, lead, nitrogen, etc.), and which metal alloy exhibits a rhenium effect. In another non-limiting embodiment, the metal alloy that is used to partially or fully form the orthopedic medical device is a refractory metal alloy. In one non-limiting embodiment, the metal alloy that is used to partially or fully form the orthopedic medical device is a stainless-steel alloy that has been modified to include at least 15 awt. % rhenium. In one non-limiting embodiment, the metal alloy that is used to partially or fully form the orthopedic medical device is a cobalt chromium alloy that has been modified to include at least 15 awt. % rhenium. In one non-limiting embodiment, the metal alloy that is used to partially or fully form the orthopedic medical device is a TiAlV alloy that has been modified to include at least 15 awt. % rhenium. In one non-limiting embodiment, the metal alloy that is used to partially or fully form the orthopedic medical device is an aluminum alloy that has been modified to include at least 15 awt. % rhenium. In one non-limiting embodiment, the metal alloy that is used to partially or fully form the orthopedic medical device is a nickel alloy that has been modified to include at least 15 awt. % rhenium. In one non-limiting embodiment, the metal alloy that is used to partially or fully form the orthopedic medical device is a titanium alloy that has been modified to include at least 15 awt. % rhenium. In one non-limiting embodiment, the metal alloy that is used to partially or fully form the orthopedic medical device is a tungsten alloy that has been modified to include at least 15 awt. % rhenium. In one non-limiting embodiment, the metal alloy that is used to partially or fully form the orthopedic medical device is a molybdenum alloy that has been modified to include at least 15 awt. % rhenium. In one non-limiting embodiment, the metal alloy that is used to partially or fully form the orthopedic medical device is a copper alloy that has been modified to include at least 15 awt. % rhenium. In one non-limiting embodiment, the metal alloy that is used to partially or fully form the orthopedic medical device is a beryllium-copper alloy that has been modified to include at least 15 awt. % rhenium.

In accordance with another and/or alternative aspect of the present disclosure, the metal alloy that is used to partially or fully form the orthopedic medical device includes rhenium and molybdenum, and the weight percent of rhenium in the metal alloy is greater than the weight percent of molybdenum in the metal alloy. In one non-limiting embodiment, the metal alloy includes rhenium and molybdenum, and the weight percent of rhenium in the metal alloy is greater than the weight percent of molybdenum in the metal alloy, and the weight percent of one or more additives (e.g., aluminum, boron, beryllium, bismuth, cadmium, calcium, cerium, chromium, cobalt, copper, gallium, gold, hafnium, iridium, iron, lanthanum, lanthanum oxide, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium) in the metal alloy is optionally greater that the weight percent of molybdenum in the metal alloy, and the metal alloy optionally includes 0-2 wt. % of a combination of other components other than the additives (e.g., carbon, oxygen, phosphorous, sulfur, hydrogen, lead, nitrogen, etc.). In one non-limiting embodiment, the metal alloy that is used to partially or fully form the orthopedic medical device includes rhenium and molybdenum, and the weight percent of rhenium plus the combined weight percent of additives is greater than the weight percent of molybdenum, and the metal alloy optionally includes 0-2 wt. % of a combination of other components other than the additives (e.g., carbon, oxygen, phosphorous, sulfur, hydrogen, lead, nitrogen, etc.)

In accordance with another and/or alternative aspect of the present disclosure, the metal alloy that is used to partially or fully form the orthopedic medical device includes rhenium and molybdenum, and the atomic weight percent of rhenium to the atomic weight percent of the combination of one or more of bismuth, niobium, tantalum, tungsten, titanium, vanadium, chromium, manganese, yttrium, zirconium, technetium, ruthenium, rhodium, hafnium, osmium, copper, and iridium is 0.4:1 to 2.5:1 (and all values and ranges therebetween).

In accordance with another and/or alternative aspect of the present disclosure, the metal alloy that is used to partially or fully form the orthopedic medical device includes at least 5 awt. % (e.g., 5-99 awt. % and all values and ranges therebetween) rhenium plus at least two metals selected from the group of molybdenum, bismuth, chromium, iridium, niobium, tantalum, titanium, yttrium, and zirconium, and the content of the metal alloy that includes other elements and compounds is 0-0.1 wt. %. In another non-limiting embodiment, the metal alloy includes rhenium, molybdenum, and chromium. In another non-limiting embodiment, the metal alloy includes at least 35 wt. % (e.g., 35-75 wt. % and all values and ranges therebetween) rhenium, and the metal alloy also includes chromium. In one non-limiting embodiment, the metal alloy includes at least 35 wt. % rhenium and at least 25 wt. % (e.g., 25-49.9 wt. % and all values and ranges therebetween) of the metal alloy includes chromium, and optionally 0.1-40 wt. % (and all values and ranges therebetween) of the metal alloy includes one or more of aluminum, boron, beryllium, bismuth, cadmium, calcium, cerium, chromium, cobalt, copper, gallium, gold, hafnium, iridium, iron, lanthanum, lanthanum oxide, lithium, magnesium, manganese, molybdenum, nickel, niobium, osmium, palladium, platinum, rare earth metals, rhodium, ruthenium, scandium, silver, silicon, tantalum, technetium, tin, titanium, tungsten, vanadium, yttrium, zinc, and/or zirconium, and the metal alloy optionally includes 0-2 wt. % (and all values and ranges therebetween) of a combination of other components other than the additives (e.g., carbon, oxygen, phosphorous, sulfur, hydrogen, lead, nitrogen, etc.). In another non-limiting embodiment, the metal alloy includes 15-50 awt. % rhenium (and all values and ranges therebetween) and 0.5-70 awt. % chromium (and all values and ranges therebetween). In another non-limiting embodiment, the metal alloy includes 15-50 awt. % rhenium (and all values and ranges therebetween) and 0.5-70 awt. % tantalum (and all values and ranges therebetween). In another non-limiting embodiment, the metal alloy includes 15-50 awt. % rhenium (and all values and ranges therebetween) and 0.5-70 awt. % niobium (and all values and ranges therebetween). In another non-limiting embodiment, the metal alloy includes 15-50 awt. % rhenium (and all values and ranges therebetween) and 0.5-70 awt. % titanium (and all values and ranges therebetween). In another non-limiting embodiment, the metal alloy includes 15-50 awt. % rhenium (and all values and ranges therebetween) and 0.5-70 awt. % zirconium (and all values and ranges therebetween). In another non-limiting embodiment, the metal alloy includes 15-50 awt. % rhenium (and all values and ranges therebetween) and 0.5-70 awt. % molybdenum (and all values and ranges therebetween). In another non-limiting embodiment, the metal alloy includes at least 15 awt. % rhenium, greater than 50 wt. % titanium (e.g., 51-80 wt. % and all values and ranges therebetween), 15-45 wt. % (and all values and ranges therebetween) niobium, 0-10 wt. % (and all values and ranges therebetween) zirconium, 0-15 wt. % (and all values and ranges therebetween) tantalum, and 0-8 wt. % molybdenum (and all values and ranges therebetween).

In accordance with another and/or alternative aspect of the present disclosure, the metal alloy that is used to partially or fully form the orthopedic medical device includes at least 0.1 wt. % (e.g., 0.1-70 wt. % and all values and ranges therebetween) rhenium and one or more metals selected from the group of molybdenum, chromium, cobalt, nickel, titanium, tantalum, niobium, zirconium, and/or tungsten. In one non-limiting embodiment, the metal alloy that is used to partially or fully form the orthopedic medical device includes at least 5 wt. % (e.g., 5-70 wt. % and all values and ranges therebetween) rhenium and one or more metals selected from the group of molybdenum, chromium, cobalt, nickel, titanium, tantalum, niobium, zirconium, and/or tungsten.

Several non-limiting examples of metal alloys that can be used to partially or fully form the orthopedic medical device are set forth below in weight percent:

| | Wt. % | | | |
|---|---|---|---|---|
| Component | Ex. 1 | Ex. 2 | Ex. 3 | Ex. 4 |
| Al | 0-35% | 0-30% | 0-25% | 0-10% |
| Bi | 0-20% | 0-20% | 0-20% | 0-20% |
| Cr | 0-60% | 0-35% | 0-30% | 0-25% |
| Co | 0-60% | 0-50% | 0-40% | 0-20% |
| Mo | 0-95% | 0-80% | 0-55% | 0-30% |
| Nb | 0-80% | 0-60% | 0-50% | 0-20% |
| Ni | 0-60% | 0-55% | 0-40% | 0-20% |
| Re | 0.1-70% | 4.5-70% | 5-70% | 5-70% |
| Ta | 0-80% | 0-50% | 0-40% | 0-25% |
| Ti | 0-60% | 0-55% | 0-40% | 0-20% |
| V | 0-20% | 0-15% | 0-10% | 0-10% |
| W | 0-80% | 0-70% | 0-50% | 0-20% |
| Y | 0-20% | 0-15% | 0-10% | 0-10% |
| Zr | 0-20% | 0-15% | 0-10% | 0-10% |

| | Wt. % | | | |
|---|---|---|---|---|
| Component | Ex. 5 | Ex. 6 | Ex. 7 | Ex. 8 |
| Ag | 0-20% | 0-20% | 0-20% | 0-20% |
| Al | 0-35% | 0-30% | 5-30% | 0-25% |
| Bi | 0-20% | 0-20% | 0-20% | 0-20% |
| Cr | 10-40% | 0-40% | 0-40% | 0-40% |
| Cu | 0-20% | 0-20% | 0-20% | 0-20% |
| Co | 10-60% | 0-60% | 0-60% | 0-60% |
| Fe | 0-80% | 30-80% | 0-80% | 0-70% |
| Hf | 0-20% | 0-20% | 0-20% | 0-20% |

-continued

| | | | | |
|---|---|---|---|---|
| Ir | 0-20% | 0-20% | 0-20% | 0-20% |
| Mg | 0-20% | 0-20% | 0-20% | 0-20% |
| Mn | 0-20% | 0-40% | 0-20% | 0-20% |
| Mo | 0-60% | 0-60% | 0-80% | 0-70% |
| Nb | 0-60% | 0-60% | 0-65% | 20-60% |
| Ni | 0-60% | 5-55% | 0-52% | 0-50% |
| Os | 0-20% | 0-20% | 0-20% | 0-20% |
| Pt | 0-20% | 0-20% | 0-20% | 0-20% |
| Re | 4.5-98% | 4.5-90% | 4.5-80% | 4.5-70% |
| Rh | 0-20% | 0-20% | 0-20% | 0-20% |
| Si | 0-20% | 0-20% | 0-20% | 0-20% |
| Sn | 0-20% | 0-20% | 0-20% | 0-20% |
| Ta | 0-60% | 0-60% | 5-65% | 0-60% |
| Tc | 0-20% | 0-20% | 0-20% | 0-20% |
| Ti | 0-60% | 0-55% | 0-53% | 0-50% |
| V | 0-20% | 0-20% | 2-20% | 0-20% |
| W | 0-60% | 0-60% | 0-80% | 0-70% |
| Y | 0-20% | 0-20% | 0-20% | 0-20% |
| Zr | 0-20% | 0-20% | 0-20% | 5-20% |

| | Wt. % | | | |
|---|---|---|---|---|
| Component | Ex. 9 | Ex. 10 | Ex. 11 | Ex. 12 |
| Ag | 0-5% | 0-5% | 0-5% | 0-5% |
| Al | 0-5% | 0-5% | 1-15% | 0-20% |
| Bi | 0-5% | 0-5% | 0-5% | 0-5% |
| Cr | 1-28% | 1-30% | 0-5% | 0-30% |
| Cu | 0-20% | 0-5% | 0-5% | 0-25% |
| Co | 0-5% | 1-60% | 0-5% | 0-60% |
| Fe | 10-80% | 0-25% | 0-5% | 0-80% |
| Hf | 0-5% | 0-5% | 0-5% | 0-5% |
| Ir | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-8% | 0-25% | 0-5% | 0-98% |
| Nb | 0-5% | 0-5% | 0-5% | 0-95% |
| Ni | 1-20% | 1-45% | 0-5% | 0-50% |
| Os | 0-5% | 0-5% | 0-5% | 0-5% |
| Pt | 0-5% | 0-5% | 0-5% | 0-5% |
| Re | 5-20% | 4.8-20% | 4.5-20% | 4.5-20% |
| Rh | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-98% |
| Tc | 0-5% | 0-5% | 0-5% | 0-5% |
| Ti | 0-5% | 0-5% | 40-93% | 0-93% |
| V | 0-5% | 0-5% | 1-10% | 0-20% |
| W | 0-5% | 0-20% | 0-5% | 0-98% |
| Y | 0-5% | 0-5% | 0-5% | 0-5% |
| Zr | 0-5% | 0-5% | 0-5% | 0-5% |

| | Wt. % | | | |
|---|---|---|---|---|
| Component | Ex. 13 | Ex. 14 | Ex. 15 | Ex. 16 |
| Mo | 35-80% | 35-80% | 35-70% | 35-65% |
| C | 0.05-0.15% | 0-0.15% | 0-0.15% | 0-0.15% |
| Hf | 0.8-1.4% | 0-2% | 0-2.5% | 0-2.5% |
| Re | 7-49% | 7-49% | 7.5-49% | 7.5-49% |
| Ta | 0-2% | 0-2% | 0-50% | 0-50% |
| W | 0-2% | 0-2% | 0-50% | 20-50% |

| | Wt. % | | | |
|---|---|---|---|---|
| Component | Ex. 17 | Ex. 18 | Ex. 10 | Ex. 20 |
| W | 20-93% | 60-92% | 20-75% | 5-98% |
| Re | 6-60% | 8-40% | 7.5-47.5% | 0-80% |
| Mo | 0-47.5% | <0.5% | 1-47.5% | 0-80% |

| | Wt. % | | | |
|---|---|---|---|---|
| Component | Ex. 21 | Ex. 22 | Ex. 23 | Ex. 24 |
| Re | 5-60% | 5-60% | 5-60% | 5-60% |
| Mo | 0-55% | 10-55% | 10-55% | 10-55% |
| Bi | 1-42 | 0-32 | 0-32 | 0-32 |
| Cr | 0-32 | 1-42 | 0-32 | 0-32 |

-continued

| | | | | |
|---|---|---|---|---|
| Ir | 0-32 | 0-32 | 1-42 | 0-32 |
| Nb | 0-32 | 0-32 | 0-32 | 1-42 |
| Ta | 0-32 | 0-32 | 0-32 | 0-32 |
| Ti | 0-32 | 0-32 | 0-32 | 0-32 |
| Y | 0-32 | 0-32 | 0-32 | 0-32 |
| Zr | 0-32 | 0-32 | 0-32 | 0-32 |

| | Wt. % | | | |
|---|---|---|---|---|
| Component | Ex. 25 | Ex. 26 | Ex. 27 | Ex. 28 |
| Re | 5-60% | 5-60% | 5-60% | 5-60% |
| Mo | 15-55% | 15-55% | 15-55% | 15-55% |
| Bi | 0-32 | 0-32 | 0-32 | 0-32 |
| Cr | 0-32 | 0-32 | 0-32 | 0-32 |
| Ir | 0-32 | 0-32 | 0-32 | 0-32 |
| Nb | 0-32 | 0-32 | 0-32 | 0-32 |
| Ta | 1-42 | 0-32 | 0-32 | 0-32 |
| Ti | 0-32 | 1-42 | 0-32 | 0-32 |
| Y | 0-32 | 0-32 | 1-42 | 0-32 |
| Zr | 0-32 | 0-32 | 0-32 | 1-42 |

| | Wt. % | | | |
|---|---|---|---|---|
| Component | Ex. 29 | Ex. 30 | Ex. 31 | Ex. 32 |
| Re | 50-75% | 55-75% | 60-75% | 65-75% |
| Cr | 25-50% | 25-45% | 25-40% | 25-35% |
| Mo | 0-25% | 0-25% | 0-25% | 0-25% |
| Bi | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |
| Ag | 0-25% | 0-25% | 0-25% | 0-25% |
| Al | 0-25% | 0-25% | 0-25% | 0-22% |
| Co | 0-25% | 0-25% | 0-25% | 0-25% |
| Fe | 0-25% | 0-25% | 0-25% | 0-25% |
| Mg | 0-25% | 0-25% | 0-25% | 0-25% |
| Ni | 0-25% | 0-25% | 0-25% | 0-25% |
| Pt | 0-25% | 0-25% | 0-25% | 0-25% |
| Si | 0-25% | 0-25% | 0-25% | 0-25% |
| Sn | 0-25% | 0-25% | 0-25% | 0-25% |

| | Wt. % | | | |
|---|---|---|---|---|
| Component | Ex. 33 | Ex. 34 | Ex. 35 | Ex. 36 |
| Re | 50-75% | 55-72% | 60-70% | 62-70% |
| Cr | 24-49% | 27-44% | 29-39% | 29-37% |
| Mo | 1-15% | 1-10% | 1-8% | 1-5% |
| Bi | 0-15% | 0-10% | 0-8% | 0-5% |
| Ir | 0-15% | 0-10% | 0-8% | 0-5% |
| Nb | 0-15% | 0-10% | 0-8% | 0-5% |
| Ta | 0-15% | 0-10% | 0-8% | 0-5% |
| V | 0-15% | 0-10% | 0-8% | 0-5% |
| W | 0-15% | 0-10% | 0-8% | 0-5% |
| Mn | 0-15% | 0-10% | 0-8% | 0-5% |
| Tc | 0-15% | 0-10% | 0-8% | 0-5% |
| Ru | 0-15% | 0-10% | 0-8% | 0-5% |
| Rh | 0-15% | 0-10% | 0-8% | 0-5% |
| Hf | 0-15% | 0-10% | 0-8% | 0-5% |
| Os | 0-15% | 0-10% | 0-8% | 0-5% |
| Cu | 0-15% | 0-10% | 0-8% | 0-5% |
| Ir | 0-15% | 0-10% | 0-8% | 0-5% |
| Ti | 0-15% | 0-10% | 0-8% | 0-5% |
| Y | 0-15% | 0-10% | 0-8% | 0-5% |

-continued

| Component | | | | |
|---|---|---|---|---|
| Zr | 0-15% | 0-10% | 0-8% | 0-5% |
| Ag | 0-15% | 0-10% | 0-8% | 0-5% |
| Al | 0-15% | 0-10% | 0-8% | 0-5% |
| Co | 0-15% | 0-10% | 0-8% | 0-5% |
| Fe | 0-15% | 0-10% | 0-8% | 0-5% |
| Mg | 0-15% | 0-10% | 0-8% | 0-5% |
| Ni | 0-15% | 0-10% | 0-8% | 0-5% |
| Pt | 0-15% | 0-10% | 0-8% | 0-5% |
| Si | 0-15% | 0-10% | 0-8% | 0-5% |
| Sn | 0-15% | 0-10% | 0-8% | 0-5% |

| | Wt. % | | | |
|---|---|---|---|---|
| Component | Ex. 37 | Ex. 38 | Ex. 39 | Ex. 40 |
| Mo | 40-95% | 40-95% | 40-95% | 40-95% |
| Co | ≤0.002% | ≤0.002% | ≤0.002% | ≤0.002% |
| Fe | ≤0.02% | ≤0.02% | ≤0.02% | ≤0.02% |
| Hf | 0.1-2.5% | 0-2.5% | 0-2.5% | 0-2.5% |
| Os | ≤1% | ≤1% | ≤1% | ≤1% |
| Nb | ≤0.01% | ≤0.01% | ≤0.01% | ≤0.01% |
| Pt | ≤1% | ≤1% | ≤1% | ≤1% |
| Re | 5-40% | 5-40% | 5-40% | 5-40% |
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| W | 0-50% | 0-50% | 0-50% | 0.5-50% |
| Zr | ≤1% | ≤1% | ≤1% | ≤1% |
| Ag | 0-5% | 0-5% | 0-5% | 0-5% |
| Al | 0-5% | 0-5% | 0-5% | 0-5% |
| Co | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |
| Sn | 0-5% | 0-5% | 0-5% | 0-5% |

| | Wt. % | | |
|---|---|---|---|
| Component | Ex. 41 | Ex. 42 | Ex. 43 |
| W | 20-95% | 60-95% | 20-80% |
| Re | 5-47.5% | 5-40% | 5-47.5% |
| Mo | 0-47.5% | <0.5% | 1-47.5% |
| Cu | <0.5% | <0.5% | <0.5% |
| Co | ≤0.002% | ≤0.002% | ≤0.002% |
| Fe | ≤0.02% | ≤0.02% | ≤0.02% |
| Hf | <0.5% | <0.5% | <0.5% |
| Os | <0.5% | <0.5% | <0.5% |
| Nb | ≤0.01% | ≤0.01% | ≤0.01% |
| Pt | <0.5% | <0.5% | <0.5% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |
| V | <0.5% | <0.5% | <0.5% |
| Zr | <0.5% | <0.5% | <0.5% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| | Wt. % | | | |
|---|---|---|---|---|
| Component | Ex. 44 | Ex. 45 | Ex. 46 | Ex. 47 |
| W | 1-94.9% | 1-94.9% | 1-94.9% | 10-95% |
| Cu | 0.1-94% | 0.1-94% | 0.1-94% | 1-84% |
| Co | ≤0.002% | ≤0.002% | ≤0.002% | ≤0.002% |
| Fe | ≤0.02% | ≤0.02% | ≤0.02% | ≤0.02% |
| Hf | 0.1-2.5% | 0-2.5% | 0-2.5% | 0-2.5% |
| Os | ≤1% | ≤1% | ≤1% | ≤1% |
| Mo | 0-5% | 0.1-3% | 0-2% | 0-3% |
| Nb | ≤0.01% | ≤0.01% | ≤0.01% | ≤0.01% |
| Pt | ≤1% | ≤1% | ≤1% | ≤1% |
| Re | 5-40% | 5-40% | 5-40% | 6-40% |

-continued

| | | | | |
|---|---|---|---|---|
| Sn | ≤0.002% | ≤0.002% | ≤0.002% | ≤0.002% |
| Ta | 0-50% | 0-50% | 0-50% | 0-50% |
| Tc | ≤1% | ≤1% | ≤1% | ≤1% |
| Ti | ≤1% | ≤1% | ≤1% | ≤1% |
| V | ≤1% | ≤1% | ≤1% | ≤1% |
| Zr | ≤1% | ≤1% | ≤1% | ≤1% |
| Ag | 0-5% | 0-5% | 0-5% | 0-5% |
| Al | 0-5% | 0-5% | 0-5% | 0-5% |
| Fe | 0-5% | 0-5% | 0-5% | 0-5% |
| Mg | 0-5% | 0-5% | 0-5% | 0-5% |
| Ni | 0-5% | 0-5% | 0-5% | 0-5% |
| Si | 0-5% | 0-5% | 0-5% | 0-5% |

| | Wt. % | | |
|---|---|---|---|
| Component | Ex. 48 | Ex. 49 | Ex. 50 |
| W | 20-96% | 25-92% | 30-88% |
| Cu | 2-74% | 2-68% | 5-62% |
| Co | ≤0.002% | ≤0.002% | ≤0.002% |
| Hf | 0-2.5% | 0-2.5% | 0-2.5% |
| Os | ≤1% | ≤1% | ≤1% |
| Mo | 0-3% | 0-2% | 0-1% |
| Nb | ≤0.01% | ≤0.01% | ≤0.01% |
| Pt | ≤1% | ≤1% | ≤1% |
| Re | 6-40% | 7-40% | 8-40% |
| Sn | ≤0.002% | ≤0.002% | ≤0.002% |
| Ta | 0-50% | 0.5-50% | 0-50% |
| Tc | ≤1% | ≤1% | ≤1% |
| Ti | ≤1% | ≤1% | ≤1% |
| V | ≤1% | ≤1% | ≤1% |
| Ag | 0-5% | 0-5% | 0-5% |
| Al | 0-5% | 0-5% | 0-5% |
| Fe | 0-5% | 0-5% | 0-5% |
| Mg | 0-5% | 0-5% | 0-5% |
| Ni | 0-5% | 0-5% | 0-5% |
| Si | 0-5% | 0-5% | 0-5% |

| | Wt. % | | | |
|---|---|---|---|---|
| Component | Ex. 51 | Ex. 52 | Ex. 53 | Ex. 54 |
| W | 25-88% | 35-87% | 40-86% | 50-85% |
| Cu | 5-68% | 5-57% | 5-51% | 5-40% |
| Hf | 0.8-1.4% | 0-2.5% | 0-2.5% | 0-2.5% |
| Re | 0-40% | 0-40% | 0-40% | 0-40% |
| Ta | 0-50% | 0-50% | 0-50% | 0-50% |

| | Wt. % | | |
|---|---|---|---|
| Component | Ex. 55 | Ex. 56 | Ex. 57 |
| Ti | 55-66% | 65-76% | 70-76% |
| Mo | 20-41% | 20-31% | 20-26% |
| Re | 4-20% | 4-20% | 4-20% |
| Yt | <0.5% | <0.5% | <0.5% |
| Nb | <0.5% | <0.5% | <0.5% |
| Co | <0.5% | <0.5% | <0.5% |
| Cr | <0.5% | <0.5% | <0.5% |
| Zr | <0.5% | <0.5% | <0.5% |

| | Wt. % | | |
|---|---|---|---|
| Component | Ex. 58 | Ex. 59 | Ex. 60 |
| W | 20-95% | 60-93% | 20-80% |
| Re | 5-47.5% | 7-40% | 5-47.5% |
| Mo | 0-47.5% | <0.5% | 1-47.5% |
| Cu | <0.5% | <0.5% | <0.5% |
| Co | ≤0.002% | ≤0.002% | ≤0.002% |
| Fe | ≤0.02% | ≤0.02% | ≤0.02% |
| Hf | <0.5% | <0.5% | <0.5% |
| Os | <0.5% | <0.5% | <0.5% |
| Nb | ≤0.01% | ≤0.01% | ≤0.01% |
| Pt | <0.5% | <0.5% | <0.5% |
| Sn | ≤0.002% | ≤0.002% | ≤0.002% |
| Ta | <0.5% | <0.5% | <0.5% |
| Tc | <0.5% | <0.5% | <0.5% |
| Ti | <0.5% | <0.5% | <0.5% |

-continued

|   | | | |
|---|---|---|---|
| V  | <0.5% | <0.5% | <0.5% |
| Zr | <0.5% | <0.5% | <0.5% |
| Ag | 0-5%  | 0-5%  | 0-5%  |
| Al | 0-5%  | 0-5%  | 0-5%  |
| Fe | 0-5%  | 0-5%  | 0-5%  |
| Mg | 0-5%  | 0-5%  | 0-5%  |
| Ni | 0-5%  | 0-5%  | 0-5%  |
| Si | 0-5%  | 0-5%  | 0-5%  |

| | Wt. % | | | |
|---|---|---|---|---|
| Component | Ex. 61 | Ex. 62 | Ex. 63 | Ex. 64 |
| Ag | 0-10%   | 0-10%   | 0-10%    | 0-10%     |
| Al | 0-10%   | 0-10%   | 0-10%    | 2-10%     |
| B  | 0-10%   | 0-10%   | 0-10%    | 0-10%     |
| Bi | 0-10%   | 0-10%   | 0-10%    | 0-10%     |
| Cr | 2-30%   | 10-30%  | 0-20%    | 0-20%     |
| Cu | 0-10%   | 0-10%   | 0-10%    | 0-10%     |
| Co | 0-10%   | 32-70%  | 0-10%    | 0-10%     |
| Fe | 50-80%  | 0-20%   | 0-10%    | 0-10%     |
| Hf | 0-10%   | 0-10%   | 0-10%    | 0-10%     |
| Ir | 0-10%   | 0-10%   | 0-10%    | 0-10%     |
| La | 0-10%   | 0-10%   | 0-10%    | 0-10%     |
| Mg | 0-10%   | 0-10%   | 0-10%    | 0-10%     |
| Mn | 0-20%   | 0-10%   | 0-10%    | 0-10%     |
| Mo | 0-10%   | 0-30%   | 0-16%    | 0-16%     |
| Nb | 0-10%   | 0-10%   | 0-10%    | 0-10%     |
| Ni | 0.1-30% | 0.1-40% | 0-10%    | 0-10%     |
| Os | 0-10%   | 0-10%   | 0-10%    | 0-10%     |
| Pt | 0-10%   | 0-10%   | 0-10%    | 0-10%     |
| Re | 5-40%   | 4.8-40% | 4.5-80%  | 4.5-80%   |
| Rh | 0-10%   | 0-10%   | 0-10%    | 0-10%     |
| Se | 0-10%   | 0-10%   | 0-10%    | 0-10%     |
| Si | 0-10%   | 0-10%   | 0-10%    | 0-10%     |
| Sn | 0-10%   | 0-10%   | 0-12%    | 0-12%     |
| Ta | 0-10%   | 0-10%   | 0-10%    | 0-10%     |
| Tc | 0-10%   | 0-10%   | 0-10%    | 0-10%     |
| Ti | 0-10%   | 0-10%   | 70-91.5% | 70-91.5%  |
| V  | 0-10%   | 0-10%   | 0-10%    | 0.01-10%  |
| W  | 0-10%   | 0-20%   | 0-10%    | 0-10%     |
| Y  | 0-10%   | 0-10%   | 0-10%    | 0-10%     |
| Zr | 0-10%   | 0-10%   | 0-10%    | 0-10%     |

| | Wt. % | | | |
|---|---|---|---|---|
| Component | Ex. 65 | Ex. 66 | Ex. 67 | Ex. 68 |
| Ag | 0-10%   | 0-10%   | 0-10%   | 0-10%   |
| Al | 0-10%   | 0-10%   | 0-10%   | 0-10%   |
| B  | 0-10%   | 0-10%   | 0-10%   | 0-10%   |
| Bi | 0-10%   | 0-10%   | 0-10%   | 0-10%   |
| Cr | 0-10%   | 0-20%   | 0-20%   | 0-10%   |
| Cu | 0-10%   | 0-10%   | 0-50%   | 0-10%   |
| Co | 0-10%   | 0-10%   | 0-10%   | 0-10%   |
| Fe | 0-10%   | 0-10%   | 0-10%   | 0-10%   |
| Hf | 0-10%   | 0-10%   | 0-10%   | 0-10%   |
| Ir | 0-10%   | 0-10%   | 0-10%   | 0-12%   |
| La | 0-10%   | 0-10%   | 0-10%   | 0-10%   |
| Mg | 0-10%   | 0-10%   | 0-10%   | 0-10%   |
| Mn | 0-10%   | 0-10%   | 0-10%   | 0-10%   |
| Mo | 0-55%   | 40-93%  | 0-50%   | 0-20%   |
| Nb | 0-10%   | 0-10%   | 0-10%   | 40-85%  |
| Ni | 0-45%   | 0-10%   | 0-10%   | 0-10%   |
| Os | 0-10%   | 0-10%   | 0-10%   | 0-10%   |
| Pt | 0-10%   | 0-10%   | 0-10%   | 0-10%   |
| Re | 14-40%  | 7-40%   | 7-40%   | 7-40%   |
| Rh | 0-10%   | 0-10%   | 0-10%   | 0-10%   |
| Se | 0-10%   | 0-10%   | 0-10%   | 0-10%   |
| Si | 0-10%   | 0-10%   | 0-10%   | 0-10%   |
| Sn | 0-10%   | 0-10%   | 0-10%   | 0-10%   |
| Ta | 35-84%  | 0-50%   | 0-50%   | 0-35%   |
| Tc | 0-10%   | 0-10%   | 0-10%   | 0-10%   |
| Ti | 0-10%   | 0-10%   | 0-10%   | 0-10%   |
| V  | 0-10%   | 0-10%   | 0-10%   | 0-10%   |
| W  | 0.1-25% | 0-50%   | 14-10%  | 0-15%   |
| Y  | 0-10%   | 0-10%   | 0-10%   | 0-10%   |
| Zr | 0-10%   | 0-10%   | 0-50%   | 0-10%   |

| | Wt. % | | | |
|---|---|---|---|---|
| Component | Ex. 69 | Ex. 70 | Ex. 71 | Ex. 72 |
| Ag | 0-10% | 0-10% | 0-5% | 0-5% |
| Al | 0-10% | 0-10% | 0-5% | 5-7% |
| B | 0-10% | 0-10% | 0-5% | 0-5% |
| Bi | 0-10% | 0-10% | 0-5% | 0-5% |
| Cr | 0-10% | 1-95% | 12-28% | 0-5% |
| Cu | 0-10% | 0-10% | 0-5% | 0-5% |
| Co | 0-10% | 0-10% | 36-68% | 0-5% |
| Fe | 0-10% | 0-10% | 0-18% | 0-5% |
| Hf | 0-10% | 0-10% | 0-5% | 0-5% |
| Ir | 0-10% | 0-10% | 0-5% | 0-5% |
| La | 0-10% | 0-10% | 0-5% | 0-5% |
| Mg | 0-10% | 0-10% | 0-5% | 0-5% |
| Mn | 0-10% | 0-10% | 0-5% | 0-5% |
| Mo | 0-10% | 0-20% | 0-12% | 0-5% |
| Nb | 0-10% | 0-10% | 0-5% | 0-5% |
| Ni | 30-58% | 0-10% | 9-36% | 0-5% |
| Os | 0-10% | 0-10% | 0-5% | 0-5% |
| Pt | 0-10% | 0-10% | 0-5% | 0-5% |
| Re | 5-40% | 5-40% | 4.8-40% | 4.5-40% |
| Rh | 0-10% | 0-10% | 0-5% | 0-5% |
| Se | 0-10% | 0-10% | 0-5% | 0-5% |
| Si | 0-10% | 0-10% | 0-5% | 0-5% |
| Sn | 0-10% | 0-10% | 0-5% | 0-5% |
| Ta | 0-10% | 0-10% | 0-5% | 0-5% |
| Tc | 0-10% | 0-10% | 0-5% | 0-5% |
| Ti | 30-58% | 0-40% | 0-5% | 70-91.5% |
| V | 0-10% | 0-10% | 0-5% | 3-6% |
| W | 0-10% | 0-10% | 0-16% | 0-5% |
| Y | 0-10% | 0-10% | 0-5% | 0-5% |
| Zr | 0-10% | 0-20% | 0-5% | 0-5% |

| | Wt. % | | | |
|---|---|---|---|---|
| Component | Ex. 73 | Ex. 74 | Ex. 75 | Ex. 76 |
| Ag | 0-8% | 0-8% | 0-8% | 0-8% |
| Al | 0-8% | 0-8% | 0-8% | 2-10% |
| B | 0-8% | 0-8% | 0-8% | 0-8% |
| Bi | 0-8% | 0-8% | 0-8% | 0-8% |
| Cr | 2-30% | 10-30% | 0-20% | 0-20% |
| Cu | 0-8% | 0-8% | 0-8% | 0-8% |
| Co | 0-8% | 32-70% | 0-8% | 0-8% |
| Fe | 50-80% | 0-20% | 0-8% | 0-8% |
| Hf | 0-8% | 0-8% | 0-8% | 0-8% |
| Ir | 0-8% | 0-8% | 0-8% | 0-8% |
| La | 0-8% | 0-8% | 0-8% | 0-8% |
| Mg | 0-8% | 0-8% | 0-8% | 0-8% |
| Mn | 0-20% | 0-8% | 0-8% | 0-8% |
| Mo | 0-8% | 0-30% | 0-16% | 0-16% |
| Nb | 0-8% | 0-8% | 0-8% | 0-8% |
| Ni | 0.1-30% | 0.1-40% | 0-8% | 0-8% |
| Os | 0-8% | 0-8% | 0-8% | 0-8% |
| Pt | 0-8% | 0-8% | 0-8% | 0-8% |
| Re | 5-40% | 4.8-40% | 4.5-80% | 4.5-80% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-12% | 0-12% |
| Ta | 0-8% | 0-8% | 0-8% | 0-8% |
| Tc | 0-8% | 0-8% | 0-8% | 0-8% |
| Ti | 0-8% | 0-8% | 70-91.5% | 70-91.5% |
| V | 0-8% | 0-8% | 0-8% | 0.01-10% |
| W | 0-8% | 0-20% | 0-8% | 0-8% |
| Y | 0-8% | 0-8% | 0-8% | 0-8% |
| Zr | 0-8% | 0-8% | 0-8% | 0-8% |

| | Wt. % | | | |
|---|---|---|---|---|
| Component | Ex. 77 | Ex. 78 | Ex. 79 | Ex. 80 |
| Ag | 0-8% | 0-8% | 0-8% | 0-8% |
| Al | 0-8% | 0-8% | 0-8% | 0-8% |
| B | 0-8% | 0-8% | 0-8% | 0-8% |
| Bi | 0-8% | 0-8% | 0-8% | 0-8% |
| Cr | 0-8% | 0-20% | 0-20% | 0-8% |

-continued

| | | | | |
|---|---|---|---|---|
| Cu | 0-8% | 0-8% | 0-50% | 0-8% |
| Co | 0-8% | 0-8% | 0-8% | 0-8% |
| Fe | 0-8% | 0-8% | 0-8% | 0-8% |
| Hf | 0-8% | 0-8% | 0-8% | 0-8% |
| Ir | 0-8% | 0-8% | 0-8% | 0-12% |
| La | 0-8% | 0-8% | 0-8% | 0-8% |
| Mg | 0-8% | 0-8% | 0-8% | 0-8% |
| Mn | 0-8% | 0-8% | 0-8% | 0-8% |
| Mo | 0-55% | 40-93% | 0-50% | 0-20% |
| Nb | 0-8% | 0-8% | 0-8% | 40-85% |
| Ni | 0-45% | 0-8% | 0-8% | 0-8% |
| Os | 0-8% | 0-8% | 0-8% | 0-8% |
| Pt | 0-8% | 0-8% | 0-8% | 0-8% |
| Re | 14-40% | 7-40% | 7-40% | 7-40% |
| Rh | 0-8% | 0-8% | 0-8% | 0-8% |
| Se | 0-8% | 0-8% | 0-8% | 0-8% |
| Si | 0-8% | 0-8% | 0-8% | 0-8% |
| Sn | 0-8% | 0-8% | 0-8% | 0-8% |
| Ta | 35-84% | 0-50% | 0-50% | 0-35% |
| Tc | 0-8% | 0-8% | 0-8% | 0-8% |
| Ti | 0-8% | 0-8% | 0-8% | 0-8% |
| V | 0-8% | 0-8% | 0-8% | 0-8% |
| W | 0.1-25% | 0-50% | 14-10% | 0-15% |
| Y | 0-8% | 0-8% | 0-8% | 0-8% |
| Zr | 0-8% | 0-8% | 0-50% | 0-8% |

| | Wt. % | | | |
|---|---|---|---|---|
| Component | Ex. 81 | Ex. 82 | Ex. 83 | Ex. 84 |
| Ag | 0-5% | 0-5% | 0-5% | 0-5% |
| Al | 0-5% | 0-5% | 0-5% | 5-7% |
| B | 0-5% | 0-5% | 0-5% | 0-5% |
| Bi | 0-5% | 0-5% | 0-5% | 0-5% |
| Cr | 0-5% | 1-95% | 12-28% | 0-5% |
| Cu | 0-5% | 0-5% | 0-5% | 0-5% |
| Co | 0-5% | 0-5% | 36-68% | 0-5% |
| Fe | 0-5% | 0-5% | 0-18% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-20% | 0-12% | 0-5% |
| Nb | 0-5% | 0-5% | 0-5% | 0-5% |
| Ni | 30-58% | 0-5% | 9-36% | 0-5% |
| Os | 0-5% | 0-5% | 0-5% | 0-5% |
| Pt | 0-5% | 0-5% | 0-5% | 0-5% |
| Re | 5-40% | 5-40% | 4.8-40% | 4.5-40% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 30-58% | 0-40% | 0-5% | 70-91.5% |
| V | 0-5% | 0-5% | 0-5% | 3-6% |
| W | 0-5% | 0-5% | 0-16% | 0-5% |
| Y | 0-5% | 0-5% | 0-5% | 0-5% |
| Zr | 0-5% | 0-20% | 0-5% | 0-5% |

| | Wt. % | | | |
|---|---|---|---|---|
| Component | Ex. 85 | Ex. 86 | Ex. 87 | Ex. 88 |
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 1-15% | 2-10% | 3-8% | 0-5% |

-continued

| | | | | |
|---|---|---|---|---|
| Nb | 0-5% | 0-5% | 0-5% | 20-45% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 1-15% |
| Tc | 0-5% | 0-5% | 0-5% | 0-5% |
| Ti | 51-70% | 51-70% | 55-70% | 51-70% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 20-40% | 22-38% | 27-33% | 1-15% |

| | Wt. % | | | |
|---|---|---|---|---|
| Component | Ex. 89 | Ex. 90 | Ex. 91 | Ex. 92 |
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 25-40% | 30-40% | 25-40% | 26-32% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 2-8% | 3-6% | 5-15% | 10-14% |
| Tc | 0-5% | 0-5% | 0-5% | 0-5% |
| Ti | 51-70% | 52-63% | 51-68% | 51-62% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-12% | 4-8% | 2-8% | 2-6% |

| | Wt. % | | | |
|---|---|---|---|---|
| Component | Ex. 93 | Ex. 94 | Ex. 95 | Ex. 96 |
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 5-35% | 10-30% | 15-25% |
| Cu | 0-5% | 0-5% | 0-5% | 0-5% |
| Co | 0-5% | 20-55% | 25-50% | 35-45% |
| Fe | 0-5% | 3-25% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 2-15% | 3-12% | 4-9% |
| Nb | 30-40% | 0-5% | 0-5% | 0-5% |
| Ni | 0-5% | 4-23% | 5-20% | 10-18% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |

-continued

| | | | | |
|---|---|---|---|---|
| Ta | 1-3% | 0-5% | 0-5% | 0-5% |
| Tc | 0-5% | 0-5% | 0-5% | 0-5% |
| Ti | 51-67% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 2-5% | 0-5% | 0-5% | 0-5% |

| | Wt. % | | | |
|---|---|---|---|---|
| Component | Ex. 97 | Ex. 98 | Ex. 99 | Ex. 100 |
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 30-65% | 40-60% | 45-55% | 0-5% |
| Nb | 0-5% | 0-5% | 0-5% | 55-99.75% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 0-5% | 0-5% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 0-5% | 0-5% |
| Y | 0-5% | 0-5% | 0-5% | 0-5% |
| Zr | 30-56% | 40-60% | 45-55% | 0.25-45% |

| | Wt. % | | | |
|---|---|---|---|---|
| Component | Ex. 101 | Ex. 102 | Ex. 103 | Ex. 104 |
| Ag | 0-5% | 0-5% | 0-5% | 0-5% |
| Al | 0-5% | 0-5% | 0-5% | 0-5% |
| B | 0-5% | 0-5% | 0-5% | 0-5% |
| Bi | 0-5% | 0-5% | 0-5% | 0-5% |
| Cr | 0-5% | 0-5% | 0-5% | 0-5% |
| Cu | 0-5% | 0-5% | 0-5% | 0-5% |
| Co | 0-5% | 0-5% | 0-5% | 0-5% |
| Fe | 0-5% | 0-5% | 0-5% | 0-5% |
| Hf | 0-5% | 0-5% | 0-5% | 0-5% |
| Ir | 0-5% | 0-5% | 0-5% | 0-5% |
| La | 0-5% | 0-5% | 0-5% | 0-5% |
| Mg | 0-5% | 0-5% | 0-5% | 0-5% |
| Mn | 0-5% | 0-5% | 0-5% | 0-5% |
| Mo | 0-5% | 0-5% | 0-5% | 0-5% |
| Nb | 75-99.5% | 95-99.25% | 55-78.5% | 68-74.25% |
| Ni | 0-5% | 0-5% | 0-5% | 0-5% |
| Os | 0-5% | 0-5% | 0-5% | 0-5% |
| Pt | 0-5% | 0-5% | 0-5% | 0-5% |
| Re | 0-5% | 0-5% | 0-5% | 0-5% |
| Rh | 0-5% | 0-5% | 0-5% | 0-5% |
| Se | 0-5% | 0-5% | 0-5% | 0-5% |
| Si | 0-5% | 0-5% | 0-5% | 0-5% |
| Sn | 0-5% | 0-5% | 0-5% | 0-5% |
| Ta | 0-5% | 0-5% | 20-35% | 25-30% |
| Tc | 0-5% | 0-5% | 0-5% | 0-5% |
| Ti | 0-5% | 0-5% | 0-5% | 0-5% |
| V | 0-5% | 0-5% | 0-5% | 0-5% |
| W | 0-5% | 0-5% | 1-8% | 0-5% |
| Y | 0-5% | 0-5% | 0-5% | 0-5% |
| Zr | 0.5-25% | 0.75-5% | 0.5-5% | 0.75-3% |

-continued

| | Wt. % | | | |
|---|---|---|---|---|
| Element | Ex. 105 | Ex. 106 | Ex. 107 | Ex. 108 |
| Re | 30-75% | 40-75% | 45-75% | 45-70% |
| Cr | 25-70% | 25-65% | 25-55% | 30-55% |
| Mo | 0-25% | 0-25% | 1-25% | 2-25% |
| Bi | 0-25% | 0-25% | 0-25% | 0-25% |
| Cr | 0-25% | 0-25% | 0-25% | 0-25% |
| Ir | 0-25% | 0-25% | 0-25% | 0-25% |
| Nb | 0-25% | 0-25% | 0-25% | 0-25% |
| Ta | 0-25% | 0-25% | 0-25% | 0-25% |
| V | 0-25% | 0-25% | 0-25% | 0-25% |
| W | 0-25% | 0-25% | 0-25% | 0-25% |
| Mn | 0-25% | 0-25% | 0-25% | 0-25% |
| Tc | 0-25% | 0-25% | 0-25% | 0-25% |
| Ru | 0-25% | 0-25% | 0-25% | 0-25% |
| Rh | 0-25% | 0-25% | 0-25% | 0-25% |
| Hf | 0-25% | 0-25% | 0-25% | 0-25% |
| Os | 0-25% | 0-25% | 0-25% | 0-25% |
| Cu | 0-25% | 0-25% | 0-25% | 0-25% |
| Ir | 0-25% | 0-25% | 0-25% | 0-25% |
| Ti | 0-25% | 0-25% | 0-25% | 0-25% |
| Y | 0-25% | 0-25% | 0-25% | 0-25% |
| Zr | 0-25% | 0-25% | 0-25% | 0-25% |

In Examples 1-108, it will be appreciated that all of the above ranges include any value between the range and any other range that is between the ranges set forth above. Any of the above values that include the ≤ symbol includes the range from 0 to the stated value and all values and ranges therebetween.

In accordance with another and/or alternative non-limiting aspect of the present disclosure, metal alloy used to partially or fully form the orthopedic medical device can optionally 1) increase the radiopacity of the orthopedic medical device, 2) increase the radial strength of the orthopedic medical device, 3) increase the yield strength and/or ultimate tensile strength of the orthopedic medical device, 4) improve the stress-strain properties of the orthopedic medical device, 5) improve the crimping and/or expansion properties of the orthopedic medical device, 6) improve the bendability and/or flexibility of the orthopedic medical device, 7) improve the strength and/or durability of the orthopedic medical device, 8) increase the hardness of the orthopedic medical device, 9) reduce the amount of recoil of the orthopedic medical device, 10) improve the biostability and/or biocompatibility properties of the orthopedic medical device, 11) increase fatigue resistance of the orthopedic medical device, 12) resist cracking and resist propagation of cracks of the orthopedic medical device, 13) reduce or eliminate the nickel and/or chromium content of orthopedic medical devices so as to reduce or eliminate problems associated with allergic reactions with surrounding tissue that can be at least partially caused by chromium and/or nickel, 14) reduce ion release of nickel and/or chromium so as to reduce or eliminate problems associated with allergic reactions with surrounding tissue that can be at least partially caused by chromium and/or nickel, 15) increased surface hardness of the orthopedic medical device, 16) reduce adverse tissue reactions after implant of the orthopedic medical device, 17) reduce metal ion release from the orthopedic medical device after implant of the orthopedic medical device, 18) reduce corrosion of the orthopedic medical device after implant of the orthopedic medical device, 19) reduce allergic reaction to the orthopedic medical device after implant of the orthopedic medical device, 20) improve hydrophilicity of the orthopedic medical device, 21) reduce magnetic susceptibility of the orthopedic medical device when implanted in a patient, and/or 22) reduce toxicity of the orthopedic medical device after implantation of the orthopedic medical device.

In accordance with another and/or alternative non-limiting aspect of the present disclosure, the metal alloy that is used to partially or fully formed the frame of the orthopedic medical device includes less than about 5 wt. % (e.g., 0-4.999999 wt. % and all values and ranges therebetween) other metals and/or impurities, typically 0-1 wt. %, more typically 0-0.1 wt. %, even more typically 0-0.01 wt. %, and still even more typically 0-0.001 wt. %. A high purity level of the metal alloy can result in the formation of a more homogeneous alloy, which in turn can result in a more uniform density throughout the metal alloy, and also can result in the desired yield and ultimate tensile strengths of the metal alloy.

In accordance with another and/or alternative aspect of the present disclosure, the orthopedic medical device is optionally subjected to one or more manufacturing processes. These manufacturing processes can include, but are not limited to, expansion, laser cutting, etching, crimping, annealing, drawing, pilgering, electroplating, electro-polishing, machining, plasma coating, 3D printing, 3D printing of printed coatings, nitriding, chemical vapor deposition, chemical polishing, cleaning, pickling, ion beam deposition or implantation, sputter coating, vacuum deposition, plasma vapor deposition, ALD, PE-CVD, etc.

In accordance with another and/or alternative non-limiting aspect of the present disclosure, the metal alloy used to partially or fully form the orthopedic medical device optionally includes a certain amount of carbon, oxygen and/or nitrogen; however, this is not required. These elements have been found to affect the forming properties, brittleness and/or ductility of some metal alloys. The controlled atomic ratio of carbon, oxygen and/or nitrogen of the metal alloy also can be used to minimize the tendency of the metal alloy to form micro-cracks during the forming of the metal alloy into the orthopedic medical device, and/or during the use and/or expansion of the orthopedic medical device in the patient. In one non-limiting embodiment, the carbon to oxygen atomic ratio can be as low as about 0.2:1 (e.g., 0.2:1 to 50:1 and all values and ranges therebetween). In one non-limiting formulation, the carbon to oxygen atomic ratio in the metal alloy is generally at least about 0.3:1. Typically the carbon content of the metal alloy is less than about 0.1 wt. % (e.g., 0-0.0999999 wt. % and all values and ranges therebetween), and more typically 0-0.01 wt. %. Carbon contents that are too large can adversely affect the physical properties of the metal alloy. Generally, the oxygen content is to be maintained at very low level. In one non-limiting formulation, the oxygen content is less than about 0.1 wt. % of the metal alloy (e.g., 0-0.0999999 wt. % and all values and ranges therebetween), and typically 0-0.01 wt. %.

In accordance with another and/or alternative aspect of the present disclosure, the metal alloy optionally includes a controlled amount of nitrogen; however, this is not required. Large amounts of nitrogen in the metal alloy can adversely affect the ductility of the metal alloy. This can in turn adversely affect the elongation properties of the metal alloy. In one non-limiting embodiment, the carbon content of the metal alloy can be less than about 0.2 wt. % (e.g., 0 wt. % to 0.1999999 wt. % and all values and ranges therebetween). In another non-limiting embodiment, the oxygen content of the metal alloy can be less than about 0.1 wt. % (e.g., 0 wt. to 0.0999999 wt. % and all values and ranges therebetween). In another non-limiting embodiment, the metal alloy can include less than about 0.001 wt. % nitrogen (e.g., 0 wt. % to 0.0009999 wt. % and all values and ranges therebetween). It is believed that the nitrogen content should be less than the content of carbon or oxygen in the metal alloy. In another non-limiting embodiment, the atomic ratio of carbon to nitrogen in the metal alloy can be at least about 1.5:1 (e.g., 1.5:1 to 400:1 and all values and ranges therebetween), and the atomic ratio of oxygen to nitrogen in the metal alloy can be at least about 1.2:1 (e.g., 1.2:1 to 150:1 and all value and ranges therebetween).

In accordance with another and/or alternative non-limiting aspect of the present disclosure, the metal alloy that is used to form all or part of the orthopedic medical device 1) is optionally not clad, metal coated, metal sprayed, plated and/or formed (e.g., cold worked, hot worked, etc.) onto another metal, or 2) does not have another metal or metal alloy metal sprayed, coated, plated, clad and/or formed onto the metal alloy. It will be appreciated that in some applications, the metal alloy of the present disclosure may be clad, metal sprayed, coated, plated and/or formed onto another metal, or another metal or metal alloy may be plated, metal sprayed, coated, clad and/or formed onto the metal alloy when forming all or a portion of the orthopedic medical device.

In accordance with another and/or alternative non-limiting aspect of the present disclosure, the metal alloy used to form all or part of the orthopedic medical device can be used to form a) a coating (e.g., cladding, dip coating, spray coating, plated coating, welded coating, plasma coating, etc.) on a portion of all of the orthopedic medical device, or b) a core of a portion or all of the orthopedic medical device. The composition of the coating, when used, can be different from the composition of the material surface to which the metal composition of the metal that is coated. The coating thickness of the metal alloy is non-limiting (e.g., 1 μm to 1 inch and all values and ranges therebetween). In one non-limiting example, the material that is to be coated is formed of chromium alloy, titanium, titanium alloy, stainless steel, iron alloy, CoCr alloy, rhenium alloy, molybdenum alloy, tungsten alloy, Ta—W alloy, refractory metal alloy, metal alloy that includes 15 awt. % rhenium, MoTa alloy, MoRe alloy, etc.), polymer material, ceramic material or composite material, and the coating layer is formed of a different material. In another non-limiting example, there is provided an orthopedic medical device wherein a core or base layer of the orthopedic medical device is formed of a metal or metal alloy (e.g., chromium alloy, titanium, titanium alloy, stainless steel, iron alloy, CoCr alloy, rhenium alloy, molybdenum alloy, tungsten alloy, Ta—W alloy, refractory metal alloy, metal alloy that includes 15 awt. % rhenium, MoTa alloy, MoRe alloy, etc.) or polymer, ceramic material, composite material, etc.), and the coating material is formed of a different metal or metal alloy that includes at least 15 awt. % rhenium. The core or material that is coated on the base layer can each form 10-99% (and all values and ranges therebetween) of the overall cross section of the orthopedic medical device. When the outer metal coating is a rhenium containing alloy, such rhenium alloy can be used to create a hard surface on the orthopedic medical device at specific locations as well as all over the surface. The base hardness of the rhenium containing alloy can be as low as 300 Vickers and/or as high as 500 Vickers (and all values and ranges therebetween). In instances where the properties of the fully annealed material are desired, but only the surface requires to be hardened, the present disclosure includes a method that can provide benefits of both a softer metal alloy with a harder outer surface or shell. As can be appreciated, other inner and outer hardness values can be used for the orthopedic medical device.

In another non-limiting embodiment, the orthopedic medical device can be partially or fully formed from a rod or tube. An inner layer of the rod (e.g., rod core, etc.) or tube can be formed of a one type of metal alloy [e.g., chromium alloy, titanium, titanium alloy, stainless steel, iron alloy, CoCr alloy, rhenium alloy, molybdenum alloy, tungsten alloy, Ta—W alloy, refractory metal alloy, MoTa alloy, MoRe alloy, etc.) and the outside of the rod or tube can be coated with one or more other materials (e.g., another type of metal or metal alloy [e.g., chromium alloy, titanium, titanium alloy, stainless steel, iron alloy, CoCr alloy, rhenium alloy, molybdenum alloy, tungsten alloy, Ta—W alloy, refractory metal alloy, MoTa alloy, MoRe alloy, etc.), polymer coating, ceramic coating, composite material coating, etc.). Non-limiting benefits of using the rhenium containing alloy in the core or interior layer of the material used to partially or fully form the orthopedic medical device can include reducing the size of the orthopedic medical device, increasing the strength of the orthopedic medical device, and/or maintaining or reducing the cost of the orthopedic medical device. As can be appreciated, the use of the rhenium containing alloy can result in other or additional advantages. The core size and/or thickness of the material used to form the core are non-limiting. The core or lower layer and the outer layer of the layered material can each form 10-99% (and all values and ranges therebetween) of the overall cross section of the layered material.

In another and/or alternative non-limiting embodiment of the disclosure, the average tensile elongation of the metal alloy used to at least partially form the orthopedic medical device is optionally at least about 20% (e.g., 20-50% average tensile elongation and all values and ranges therebetween). The desired tensile elongation can be obtained from a unique combination of the metals in the metal alloy in combination with achieving the desired purity and composition of the alloy and the desired grain size of the metal alloy.

In accordance with another and/or alternative non-limiting aspect of the present disclosure, the orthopedic medical device can be at least partially (e.g., 1-99.999 wt. % and all values and ranges therebetween) or fully formed from by 3D printing, and/or a swaging process; however, this is not required. In one non-limiting embodiment, swaging is performed on the metal alloy to at least partially or fully achieve final dimensions of one or more portions of the orthopedic medical device. The swaging dies can be shaped to fit the final dimension of the orthopedic medical device; however, this is not required.

In accordance with another and/or alternative non-limiting aspect of the present disclosure, the metal alloy can optionally be nitrided; however, this is not required. The nitrided layer on the metal alloy can function as a lubricating surface during the optional drawing of the metal alloy when partially or fully forming the orthopedic medical device.

In accordance with another and/or alternative non-limiting aspect of the present disclosure, the orthopedic medical device can optionally be partially (e.g., 1% to 99.99% and all values and ranges therebetween) or fully be coated with and/or include one or more agents. When one or more agents are coated on the orthopedic medical device, and the orthopedic medical device includes an enhancement coating, one or more agents are generally coated on the outer surface of the enhancement coating. The term "agent" includes, but is not limited to a substance, pharmaceutical, biologic, veterinary product, drug, and analogs or derivatives otherwise formulated and/or designed to prevent, inhibit and/or treat one or more clinical and/or biological events, and/or to promote healing. Non-limiting examples of clinical events that can be addressed by one or more agents include, but are not limited to, viral, fungus and/or bacterial infection; vascular diseases and/or disorders; lymphatic diseases and/or disorders; cancer; implant rejection; pain; nausea; swelling; organ failure; immunity diseases and/or disorders; cell growth inhibitors, blood diseases and/or disorders; heart diseases and/or disorders; neuralgia diseases and/or disorders; fatigue; genetic diseases and/or disorders; trauma; cramps; muscle spasms; tissue repair; nerve repair; neural regeneration and/or the like.

The type and/or amount of agent included coated on frame for an orthopedic medical device can vary. In accordance with another and/or alternative aspect of the present disclosure, one or more portions of the frame for an orthopedic medical device can optionally 1) include the same or different agents, 2) include the same or different amount of one or more agents, 3) include the same or different polymer coatings, 4) include the same or different coating thicknesses of one or more polymer coatings, 5) have one or more portions of the frame for an orthopedic medical device controllably release and/or uncontrollably release one or more agents, and/or 6) have one or more portions of the frame for an orthopedic medical device controllably release one or more agents and one or more portions of the frame for an orthopedic medical device uncontrollably release one or more agents.

In accordance with another and/or alternative aspect of the present disclosure, one or more surfaces of the frame for an orthopedic medical device can optionally be treated to achieve the desired coating properties of the one or more agents and/or one or more polymers coated on the frame for an orthopedic medical device. Such surface treatment techniques include, but are not limited to, cleaning, buffing, smoothing, nitriding, annealing, swaging, cold working, etching (chemical etching, plasma etching, etc.), etc. As can be appreciated, other or additional surface treatment processes can be used prior to the coating of one or more agents and/or polymers on the surface of the frame for an orthopedic medical device.

In another and/or alternative non-limiting aspect of the disclosure, the orthopedic medical device can optionally include a marker material that facilitates enabling the orthopedic medical device to be properly positioned in a body passageway. The marker material is typically designed to be visible to electromagnetic waves (e.g., x-rays, microwaves, visible light, infrared waves, ultraviolet waves, etc.); sound waves (e.g., ultrasound waves, etc.); magnetic waves (e.g., MRI, etc.); and/or other types of electromagnetic waves (e.g., microwaves, visible light, infrared waves, ultraviolet waves, etc.).

In accordance with another and/or alternative aspect of the present disclosure, the orthopedic medical device or one or more regions of the orthopedic medical device can optionally be constructed by use of one or more microelectromechanical manufacturing (MEMS) techniques (e.g., micro-machining, laser micro-machining, micro-molding, etc.); however, other or additional manufacturing techniques can be used.

In accordance with another and/or alternative aspect of the present disclosure, the orthopedic medical device can optionally include one or more surface structures (e.g., pore, channel, pit, rib, slot, notch, bump, teeth, needle, well, hole, groove, etc.). These structures can be at least partially formed by MEMS (e.g., micro-machining, etc.) technology and/or other types of technology.

In accordance with another and/or alternative aspect of the present disclosure, the orthopedic medical device can optionally include one or more micro-structures (e.g., micro-needle, micro-pore, micro-cylinder, micro-cone, micro-pyramid, micro-tube, micro-parallelopiped, micro-prism, micro-hemisphere, teeth, rib, ridge, ratchet, hinge, zipper, zip-tie like structure, etc.) on the surface of the orthopedic medical device. As defined herein, a "micro-structure" is a structure having at least one dimension (e.g., average width, average diameter, average height, average length, average depth, etc.) that is no more than about 2 mm, and typically no more than about 1 mm. Non-limiting examples of structures that can be formed on the one or more portions of the orthopedic medical device are illustrated in U.S. Pat. Nos. 7,255,710 and 7,141,063, which are incorporated herein by reference.

In accordance with another and/or alternative aspect of the present disclosure, there is optionally provided a near net process for the orthopedic medical device. In one non-limiting embodiment of the disclosure, there is provided a method of powder pressing materials and increasing the strength post-sintering by imparting additional cold work. In one non-limiting embodiment, the green part is pressed and then sintered. Thereafter, the sintered part is again pressed to increase its mechanical strength by imparting cold work into the pressed and sintered part.

In accordance with another and/or alternative aspect of the present disclosure, the metal alloy used to at least partially or fully form the orthopedic medical device can optionally be initially formed into a blank, a rod, a tube, etc., and then finished into final form by one or more finishing processes. The metal alloy blank, rod, tube, etc., can be formed by various techniques such as, but not limited to, 1) melting the metal alloy and/or metals that form the metal alloy (e.g., vacuum arc melting, etc.) and then extruding and/or casting the metal alloy into a blank, rod, tube, etc., 2) melting the metal alloy and/or metals that form the metal alloy, forming a metal strip, and then rolling and welding the strip into a blank, rod, tube, etc., 3) consolidating the metal powder of the metal alloy and/or metal powder of metals that form the metal alloy into a blank, rod, tube, etc., or 4) 3-D printing the metal powder of the metal alloy and/or metal powder of metals that form the metal alloy into a blank, rod, tube, etc. When the metal alloy is formed into a blank, the shape and size of the blank is non-limiting.

In accordance with another and/or alternative aspect of the present disclosure, when the metal powder is consolidated to form the metal alloy into a blank, rod, tube, etc., the metal powder is pressed together to form a solid solution of the metal alloy into a near net frame for an orthopedic medical device, near net component of the orthopedic medical device, blank, rod, tube, etc. Typically, the pressing process is by an isostatic process (i.e., uniform pressure applied from all sides on the metal powder); however other processes can be used. When the metal powders are pressed together isostatically, cold isostatic pressing (CIP) is typically used to consolidate the metal powders; however, this is not required. The pressing process can be performed in an inert atmosphere, an oxygen-reducing atmosphere (e.g., hydrogen, argon and hydrogen mixture, etc.), and/or under a vacuum; however, this is not required.

In accordance with another and/or alternative aspect of the present disclosure, when metal powder is used to 3D print the orthopedic medical device, component of the orthopedic medical device, blank, rod, tube, etc., the average particle size of the metal powder is optionally 2-62 microns, and more particularly about 5-49.9 microns, the average density of the metal powders is greater than 5 g/cm$^3$, and the metal powder is generally spherical-shaped, and the Hall flow (s/50 g) is less than 30 seconds (e.g., 2-29.99 seconds and all values and ranges therebetween). In another non-limiting embodiment of the disclosure, the average tensile elongation of the metal alloy used to partially or fully form the orthopedic medical device is optionally at least about 25% (e.g., 25%-50% average tensile elongation and all values and ranges therebetween).

In accordance with another and/or alternative non-limiting aspect of the present disclosure, the orthopedic medical device can be partially (e.g., 1% to 99.99% and all values and ranges therebetween) or fully be coated with an enhancement coating to improve one or more properties of the orthopedic medical device (e.g., change exterior color of material having coated surface, increase surface hardness by use of the coated surface, increase surface toughness material having coated surface, reduced friction via use of the coated surface, improve scratch resistance of material that has the coated surface, improve impact wear of coated surface, improve resistance to corrosion and oxidation of coated material, form a non-stick coated surface, improve biocompatibility of material having the coated surface, reduce toxicity of material having the coated surface, reduce ion release from material having the coated surface, the enhancement coating forms a surface that is less of an irritant to cell about the coated surface after the orthopedic medical device is implanted, reduces the rate to which cells grown on coated surface after orthopedic medical device is implanted, forms or promotes the formation of nitric oxide (NO), reduces bacterial growth and/or infection, forms an outer surface that is absent nickel and/or chromium, promotes bone healing about the orthopedic medical device after implantation of the orthopedic medical device. Non-limiting enhancement coatings that can be applied to a portion or all of the outer surface of the orthopedic medical device includes chromium nitride (CrN), diamond-like carbon (DLC), titanium nitride (TiN), titanium oxynitride or titanium nitride oxide (TiNOx), zirconium nitride (ZrN), zirconium oxide (ZrO$_2$), zirconium oxynitride (ZrNxOy) [e.g., cubic ZrN:O, cubic ZrO$_2$:N, tetragonal ZrO$_2$:N, and monoclinic ZrO$_2$:N phase coatings], oxyzirconium-nitrogen-carbon (ZrNC), zirconium OxyCarbide (ZrOC), and combinations of such coatings. In one non-limiting embodiment, the one or more enhancement coatings are optionally applied to a portion or all of the outer surface of orthopedic medical device by a vacuum process using an energy source to vaporize material and deposit a thin layer of enhancement coating material. Such vacuum coating process, when used, can include a physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process. In one non-limiting embodiment, the coating process is one or more of a PVD, CVD, ALD and PE-CVD, and wherein the coating process occurs at a temperature of 200-400° C. (and all values and ranges therebetween) for at least 10 minutes (e.g., 10-400 minutes and all values and ranges therebetween). In another non-limiting embodiment, the coating process is one or more of a PVD, CVD, ALD and PE-CVD, and wherein the coating process occurs at a temperature of 220-300° C. for 60-120 minutes. In another non-limiting embodiment, when the materials of the one or more enhancement coatings are to be applied to the outer surface of the orthopedic medical device that is partially or fully formed of a metal alloy, the materials of the one or more enhancement coatings can optionally be combine with one or more metals in the metal alloy, and/or combined with nitrogen, oxygen, carbon, or other elements that are in the metal alloy and/or present in the atmosphere about the metal alloy to a form an enhancement coating on the outer surface of the metal alloy. In another non-limiting embodiment, when the materials of the one or more enhancement coatings are to be applied to the outer surface of the orthopedic medical device that is partially or fully formed of a metal alloy, the materials of the one or more enhancement coatings can optionally be used to form various coating colors on the outer surface of the metal alloy (e.g., gold, copper, brass, black, rose gold, chrome, blue, silver, yellow, green, etc.). In another non-limiting embodiment, the thickness of the enhancement coating is greater than 1 nanometer (e.g., 2 nanometers to 100 microns and all values and ranges therebetween), and typically 0.1-25 microns, and more typically 0.2-10 microns. In another non-limiting embodiment, the hardness of the enhancement coating can be at least 5 GPa (ASTM C1327-15 or ASTM C1624-05), typically 5-50 GPa (and all values and ranges therebetween), more typically 10-25 GPa, and still more typically 14-24 GPa. In another non-limiting embodiment, the coefficient of friction (COF) of the enhancement coating can be 0.04-0.2 (and all values and ranges therebetween), and typically 0.6-0.15. In another non-limiting embodiment, the wear rate of the enhancement coating can be $0.5 \times 10^{-7}$ mm$^3$/N-m to $3 \times 10^{-7}$ mm$^3$/N-m (an all values and ranges therebetween), and typically $1.2 \times 10^{-7}$ mm$^3$/N-m to $2 \times 10^{-7}$ mm$^3$/N-m. In another non-limiting embodiment, silicon-based precursors (e.g., trimethylsilane, tetramethylsilane, hexachlorodisilane, silane, dichlorosilane, trichlorosilane, silicon tetrachloride, tris(dimethylamino) silane, bis(tert-butylamino)silane, trisilylamine, allyltrimethoxysilane, (3-aminopropyl)triethoxysilane, butyltrichlorosilane, n-sec-butyl(trimethylsilyl)amine, chloropentamethyldisilane, 1,2-dichlorotetramethyldisilane, [3-(diethylamino)propyl]trimethoxysilane, 1,3-diethyl-1,1,3,3-tetramethyldisilazane, dimethoxydimethylsilane, dodecamethylcyclohexasilane, hexamethyldisilane, isobutyl (trimethoxy)silane, methyltrichlorosilane, 2,4,6,8,10-pentamethylcyclopentasiloxane, pentamethyldisilane, n-propyltriethoxysilane, silicon tetrabromide, silicon tetrabromide, etc.) can optionally be used to facilitate in the application of the enhancement coating to one or more portions or all of the orthopedic medical device. In one non-limiting embodiment, the enhancement coating includes no more than 0.1 wt. % nickel, no more than 0.1 wt. % chromium, and/or no more than 0.1 wt. % cobalt. In another non-limiting embodiment, the outer surface of the orthopedic medical device includes no more than 0.1 wt. % nickel, no more than 0.1 wt. % chromium, and/or no more than 0.1 wt. % cobalt. The adhesion layer includes no more than 0.1 wt. % nickel, no more than 0.1 wt. % chromium, and/or no more than 0.1 wt. % cobalt.

In accordance with another and/or alternative non-limiting aspect of the present disclosure, the orthopedic medical device can be partially or fully coated with an enhancement coating composition that includes a chromium nitride (CrN) coating. A portion or all of the outer surface of the orthopedic medical device can be partially or fully coated with the chromium nitride (CrN) coating. The enhancement coating can be used to improve hardness, improve toughness, reduced friction, resistant impact wear, improve resistance to corrosion and oxidation, and/or form a reduced stick surface when in contact with many different materials. In accordance with one non-limiting embodiment, the chromium nitride (CrN) coating generally includes 40-85 wt. % Cr (and all values and ranges therebetween), 15-60 wt. % N (and all values and ranges therebetween), 0-10 wt. % Re (and all values and ranges therebetween), 0-10 wt. % Si (and all values and ranges therebetween), 0-2 wt. % O (and all values and ranges therebetween), and 0-2 wt. % C (and all values and ranges therebetween). In one non-limiting coating process, all or a portion of the outer surface of the orthopedic medical device are initially coated with Cr metal. The Cr metal coating can be applied by PVD, CVD, ALD and PE-CVD in an inert environment. The coating thickness of Cr metal is 0.5-15 microns. Thereafter, the Cr metal coating is exposed to nitrogen gas and/or a nitrogen containing gas compound to cause the nitrogen to react with the Cr metal coating to form a layer of CrN on the outer surface of the Cr metal coating and/or the outer surface of the orthopedic medical device. Particles of Cr metal can optionally be mixed with nitrogen gas and/or a nitrogen containing gas compound to facilitate in the formation of the CrN coating. When Cr metal particles are used, the initial Cr coating layer on the outer surface of the orthopedic medical device can optionally be eliminated. In another non-limiting embodiment, the enhancement coating composition generally includes 65-80 wt. % Cr, 15-30 wt. % N, 0-8 wt. % Re, 0-1 wt. % Si, 0-1 wt. % O, and 0-1 wt. % C.

In accordance with another and/or alternative non-limiting aspect of the present disclosure, the orthopedic medical device can be partially or fully coated with an enhancement coating composition that includes a diamond-Like Carbon (DLC) coating. A portion or all of the outer surface of the orthopedic medical device can be partially or fully coated with the diamond-Like Carbon (DLC) coating. The enhancement coating can be used to improve hardness, improve toughness, reduced friction, resistant impact wear, improve resistance to corrosion and oxidation, improve biocompatibility, and/or form a reduced stick surface when in contact with many different materials. In one non-limiting embodiment, the diamond-Like Carbon (DLC) coating generally includes 60-99.99 wt. % C (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % O (and all values and ranges therebetween). The carbon coating can be applied by PVD, CVD, ALD and PE-CVD in an inert environment. The carbon layer can be applied by use of methane and/or acetylene gas; however, other or additional carbon sources can be used. The coating thickness of the carbon is 0.5-15 microns. In another non-limiting embodiment, all or a portion of the outer surface of the orthopedic medical device are coated with the enhancement coating composition that generally includes 90-99.99 wt. % C, 0-1 wt. % N, 0-8 wt. % Re, 0-1 wt. % Si, and 0-1 wt. % O.

In accordance with another and/or alternative non-limiting aspect of the present disclosure, the orthopedic medical device can be partially or fully coated with an enhancement coating composition that includes a titanium nitride (TiN) coating. A portion or all of the outer surface of the orthopedic medical device can include the titanium nitride (TiN) coating. The enhancement coating can be used to improve hardness, improve toughness, improve resistance to corrosion and oxidation, reduced friction, and/or form a reduced stick surface when in contact with many different materials. In one non-limiting embodiment, all or a portion of the outer surface of the orthopedic medical device are optionally initially coated with Ti metal. The Ti metal coating, when applied, can be applied by PVD, CVD, ALD and PE-CVD in an inert environment. The coating thickness of Ti metal is 0.05-15 microns (and all values and ranges therebetween). As can be appreciated, the initial Ti coating is optional. Thereafter, the Ti metal coating, when applied, is exposed to nitrogen gas and/or a nitrogen containing gas compound and optionally titanium particles to cause the nitrogen to react with the Ti metal coating and/or titanium metal particles to form a layer of TiN on the outer surface of the Ti metal coating and/or the outer surface of the orthopedic medical device. If a titanium layer is not preapplied, the TiN coating can be formed by exposing the outer surface of the orthopedic medical device to titanium particles and nitrogen gas and/or a nitrogen containing gas compound. The coating thickness of the TiN coating is generally at least 0.1 microns (e.g., 0.1-15 microns and all values and ranges therebetween), and typically 0.2-2 microns.

In accordance with another and/or alternative non-limiting aspect of the present disclosure, the orthopedic medical device can be partially or fully coated with an enhancement coating composition that includes a titanium oxynitride or titanium nitride oxide (TiNOx) coating. A portion or all of the outer surface of the orthopedic medical device can include the titanium oxynitride or titanium nitride oxide (TiNOx) coating. The enhancement coating can be used to improve hardness, improve toughness, improve resistance to corrosion and oxidation, reduced friction, and/or form a reduced stick surface when in contact with many different materials, improve biocompatibility, reduce infection, reduce bacterial growth, and/or promote nitric oxide formation on the surface of the coating. In one non-limiting embodiment, all or a portion of the outer surface of the orthopedic medical device are optionally initially coated with Ti metal. The Ti metal coating, when applied, can be applied by PVD, CVD, ALD and PE-CVD in an inert environment. The coating thickness of Ti metal is 0.05-15 microns (and all values and ranges therebetween). As can be appreciated, the initial Ti coating is optional. Thereafter, the Ti metal coating is exposed to titanium particles and a nitrogen and oxygen mixture that can include nitrogen gas, oxygen gas, a nitrogen containing gas compound and/or an oxygen containing gas compound to cause the nitrogen and oxygen to react with the Ti metal coating, if such coating is used, and/or with the Ti metal particles to form a layer of TiNOx on the outer surface of the Ti metal coating and/or the outer surface of the orthopedic medical device. The ratio of the N to the O can be varied to control the amount of O in the TiNOx coating. If a titanium layer is not preapplied, the TiNOx coating can be formed by exposing the outer surface of the orthopedic medical device to titanium particles and a nitrogen and oxygen source such as nitrogen gas, oxygen gas, a nitrogen containing gas compound and/or an oxygen containing gas compound. The ratio of N to O when forming the TiNOx coating is generally 1:10 to 10:1 (and all values and ranges therebetween). The coating thickness of the TiNOx coating is generally at least 0.1 microns (e.g., 0.115 microns and all values and ranges therebetween), and typically 0.2-2 microns. In another non-limiting embodiment, a TiNOx coating is applied to a portion or all of the outer surface of the orthopedic medical device, and the TiNOx coating is formed by a) exposing the outer surface of a portion of all of the orthopedic medical device to Ti particles (PVD, CVD, ALD and PE-CVD process) and/or a Ti containing solution to form a Ti layer on a portion of all of the orthopedic medical device, and wherein the thickness of the Ti coating is 0.05-5 microns, and b) exposing the Ti coating to a nitrogen and oxygen source such as nitrogen gas, oxygen gas, a nitrogen containing gas compound and/or an oxygen containing gas compound to form a TiNOx coating, and wherein ratio of N to O when forming the TiNOx coating is generally 1:10 to 10:1, and wherein the coating thickness of the TiNOx coating is 0.2-5 microns. In another non-limiting embodiment, a TiNOx coating is applied to a portion or all of the outer surface of the orthopedic medical device, and the TiNOx coating is formed by exposing a portion or all of the outer surface of the orthopedic medical device to Ti particles and a nitrogen and oxygen source such as nitrogen gas, oxygen gas, a nitrogen containing gas compound and/or an oxygen containing gas compound to form a TiNOx coating, and wherein ratio of N to O when forming the TiNOx coating is generally 1:10 to 10:1, and wherein the coating thickness of the TiNOx coating is 0.2-5 microns. In another non-limiting embodiment, the enhancement coating composition generally includes 20-85 wt. % Ti (and all values and ranges therebetween), 0.5-35 wt. % N (and all values and ranges therebetween), 0-10 wt. % Re (and all values and ranges therebetween), and 0.5-35 wt. % O (and all values and ranges therebetween). In another non-limiting embodiment, a coating of TiNOx was formed on the orthopedic medical device by reactive physical vapor deposition in a vacuum chamber. Depending on the oxygen-nitrogen ratio during vapor deposition, a coating deposit of TiNOx with defined composition and resistivity can be coated on the outer surface of the orthopedic medical device.

In accordance with another and/or alternative non-limiting aspect of the present disclosure, the orthopedic medical device can be partially or fully coated with an enhancement coating composition that includes a zirconium nitride (ZrN) coating. The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the orthopedic medical device is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to nitrogen gas and/or a nitrogen containing gas compound to cause the nitrogen to react with the Zn metal coating to form a layer of ZrN on the outer surface of the Zr metal coating and/or the outer surface of the orthopedic medical device. Particles of Zr metal can optionally be mixed with nitrogen gas and/or a nitrogen containing gas compound to facilitate in the formation of the ZrN coating. When Zr metal particles are used, the initial Zr coating layer on the outer surface of the orthopedic medical device can optionally be eliminated. The ZrN coating has been found to produce a gold-colored enhancement coating color. In another non-limiting embodiment, the enhancement coating composition generally includes 35-90 wt. % Zr (and all values and ranges therebetween), 5-25 wt. % N (and all values and ranges therebetween), 0-10 wt. % Re (and all values and ranges therebetween), 0-20 wt. % Si (and all values and ranges therebetween), 0-2 wt. % O (and all values and ranges therebetween), and 0-2 wt. % C (and all values and ranges therebetween). In another non-limiting embodiment, the enhancement coating composition generally includes 80-90 wt. % Zr, 10-20 wt. % N, 0-8 wt. % Re, 0-1 wt. % Si, 0-1 wt. % O, and 0-1 wt. % C.

In accordance with another and/or alternative non-limiting aspect of the present disclosure, the orthopedic medical device can be partially or fully coated with an enhancement coating composition that includes a zirconium oxide ($ZrO_2$) coating. The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the orthopedic medical device is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to oxygen gas and/or oxygen containing gas compound to cause the oxygen to react with the Zn metal coating to form a layer of zirconium oxide ($ZrO_2$) on the outer surface of the Zr metal coating and/or the outer surface of the orthopedic medical device. Particles of Zr metal can optionally be mixed with oxygen gas and/or an oxygen containing gas compound to facilitate in the formation of the $ZrO_2$ coating. When Zr metal particles are used, the initial Zr coating layer on the outer surface of the orthopedic medical device can optionally be eliminated. The zirconium oxide ($ZrO_2$) coating has been found to produce a blue colored enhancement coating color. In another non-limiting embodiment, the enhancement coating composition generally includes 35-90 wt. % Zr (and all values and ranges therebetween), 10-35 wt. % O (and all values and ranges therebetween), 0-2 wt. % N (and all values and ranges therebetween), 0-10 wt. % Re (and all values and ranges therebetween), 0-20 wt. % Si (and all values and ranges therebetween), and 0-2 wt. % C (and all values and ranges therebetween). In another non-limiting embodiment, the enhancement coating composition generally includes 70-80 wt. % Zr, 20-30 wt. %, 0-1 wt. % N, 0-8 wt. % Re, 0-1 wt. % Si, and 0-1 wt. % C.

In accordance with another and/or alternative non-limiting aspect of the present disclosure, the orthopedic medical device can be partially or fully coated with an enhancement coating composition that includes both a zirconium oxide ($ZrO_2$) coating and a zirconium nitride coating (ZrN). The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to a) both oxygen gas and/or oxygen containing gas compound and also to nitrogen gas and/or nitrogen containing gas compound, b) nitrogen gas and/or nitrogen containing gas compound and then to oxygen gas and/or oxygen containing gas compound, or c) oxygen gas and/or oxygen gas containing compound and then to nitrogen gas and/or nitrogen gas containing compound. The coating composition of the zirconium oxide ($ZrO_2$) coating and the zirconium nitride coating (ZrN) are similar or the same as discussed above. As discussed above, Particles of Zr metal can optionally be mixed with oxygen gas and/or an oxygen containing gas compound to facilitate in the formation of the $ZrO_2$ coating and the nitrogen gas and/or nitrogen gas containing compound to facilitate in the formation of the ZrN coating. When Zr metal particles are used, the initial Zr coating layer on the outer surface of the orthopedic medical device can optionally be eliminated.

In accordance with another and/or alternative non-limiting aspect of the present disclosure, the orthopedic medical device can be partially or fully coated with an enhancement coating composition that includes a zirconium oxycarbide (ZrOC) coating. The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the metal alloy is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to a) both to oxygen gas and/or an oxygen containing gas compound and to carbon and/or a carbon containing gas compound (e.g., methane and/or acetylene gas), b) carbon and/or a carbon containing gas compound and then to oxygen gas and/or an oxygen containing gas compound, or c) oxygen gas and/or oxygen containing gas compound and then to carbon and/or carbon containing gas compound. Particles of Zr metal can optionally be mixed with oxygen gas and/or an oxygen containing gas compound and the carbon and/or carbon containing gas compound to facilitate in the formation of the zirconium oxycarbide (ZrOC) coating. When Zr metal particles are used, the initial Zr coating layer on the outer surface of the orthopedic medical device can optionally be eliminated. In another non-limiting embodiment, the enhancement coating composition generally includes 40-95 wt. % Zr (and all values and ranges therebetween), 5-25 wt. % O (and all values and ranges therebetween), and 10-40 wt. % C (and all values and ranges therebetween), 0-2 wt. % N (and all values and ranges therebetween), 0-10 wt. % Re (and all values and ranges therebetween), and 0-20 wt. % Si (and all values and ranges therebetween). In another non-limiting embodiment, the enhancement coating composition generally includes 40-65 wt. % Zr, 5-25 wt. % O, and 25-40 wt. % C, 0-1 wt. % N, 0-8 wt. % Re, and 0-1 wt. % Si.

In accordance with another and/or alternative non-limiting aspect of the present disclosure, the orthopedic medical device can be partially or fully coated with an enhancement coating composition that includes a zirconium oxynitride (ZrNxOy) [e.g., cubic ZrN:O, cubic $ZrO_2$:N, tetragonal $ZrO_2$:N, and monoclinic $ZrO_2$:N phase coatings]. A portion or all of the outer surface of the orthopedic medical device can include the zirconium oxynitride (ZrNxOy). The enhancement coating can be used to improve hardness, improve toughness, improve resistance to corrosion and oxidation, reduced friction, form a reduced stick surface when in contact with many different materials, improve biocompatibility, reduce infection, reduce bacterial growth, and/or promote nitric oxide formation on the surface of the coating. In one non-limiting embodiment, all or a portion of the outer surface of the orthopedic medical device are optionally initially coated with Zr metal. The Zr metal coating, when applied, can be applied by PVD, CVD, ALD and PE-CVD in an inert environment. The coating thickness of Zr metal is 0.05-15 microns (and all values and ranges therebetween). As can be appreciated, the initial Zr coating is optional. Thereafter, the Zr metal coating is exposed to zirconium particles and a nitrogen and oxygen mixture that can include nitrogen gas, oxygen gas, a nitrogen containing gas compound and/or an oxygen containing gas compound to cause the nitrogen and oxygen to react with the Zr metal coating, if such coating is used, and/or with the Zr metal particles to form a layer of ZrNxOy on the outer surface of the Zr metal coating and/or the outer surface of the orthopedic medical device. The ratio of the N to the O can be varied to control the amount of O and N in the ZrNxOy coating. If a zirconium layer is not preapplied, the ZrNxOy coating can be formed by exposing the outer surface of orthopedic medical device to zirconium particles and a nitrogen and oxygen source such as nitrogen gas, oxygen gas, a nitrogen containing gas compound and/or an oxygen containing gas compound. The ratio of N to O when forming the ZrNxOy coating is generally 1:10 to 10:1 (and all values and ranges therebetween). The coating thickness of the ZrNxOy coating is generally at least 0.1 microns (e.g., 0.1-15 microns and all values and ranges therebetween), and typically 0.2-2 microns. In another non-limiting embodiment, a ZrNxOy coating is applied to a portion or all of the outer surface of the orthopedic medical device, and the ZrNxOy coating is formed by a) exposing the outer surface of a portion of all of the orthopedic medical device to Zr particles (PVD, CVD, ALD and PE-CVD process) and/or a Zr containing solution to form a Zr layer on a portion of all of the orthopedic medical device, and wherein the thickness of the Zr coating is 0.05-5 microns, and b) exposing the Zr coating to a nitrogen and oxygen source such as nitrogen gas, oxygen gas, a nitrogen containing gas compound and/or an oxygen containing gas compound to form a ZrNxOy coating, and wherein ratio of N to O when forming the ZrNxOy coating is generally 1:10 to 10:1, and wherein the coating thickness of the ZrNxOy coating is 0.2-5 microns. In another non-limiting embodiment, a ZrNxOy coating is applied to a portion or all of the outer surface of the orthopedic medical device, and the ZrNxOy coating is formed by exposing a portion or all of the outer surface of the orthopedic medical device to Zr particles and a nitrogen and oxygen source such as nitrogen gas, oxygen gas, a nitrogen containing gas compound and/or an oxygen containing gas compound to form a ZrNxOy coating, and wherein ratio of N to O when forming the ZrNxOy coating is generally 1:10 to 10:1, and wherein the coating thickness of the ZrNxOy coating is 0.2-5 microns. In another non-limiting embodiment, the enhancement coating composition generally includes 20-85 wt. % Zr (and all values and ranges therebetween), 0.5-35 wt. % N (and all values and ranges therebetween), and 0.5-35 wt. % O (and all values and ranges therebetween). In another non-limiting embodiment, a coating of ZrNxOy was formed on the orthopedic medical device by reactive physical vapor deposition in a vacuum chamber. Depending on the oxygen-nitrogen ratio during vapor deposition, a coating deposit of ZrNxOy with defined composition and resistivity can be coated on the outer surface of the orthopedic medical device.

In accordance with another and/or alternative non-limiting aspect of the present disclosure, the orthopedic medical device can be partially or fully coated with an enhancement coating composition that includes a zirconium-nitrogen-carbon (ZrNC) coating. The enhancement coating can be used to improve hardness, improve toughness, improve resistance to corrosion and oxidation, reduced friction, and/or form a reduced stick surface when in contact with many different materials. In one non-limiting embodiment all or a portion of the outer surface of the orthopedic medical device is initially coated with Zr metal. The Zr metal coating can be applied by PVD, CVD, ALD and PE-CVD in an inert environment. The coating thickness of Zr metal is 0.5-15 microns. Thereafter, the Zr metal coating is exposed to nitrogen gas and/or a nitrogen containing gas compound and then to carbon and/or a carbon containing gas compound (e.g., methane and/or acetylene gas). The color of the ZrNC will vary depending on the amount of C and N in the coating. Particles of Zr metal can optionally be mixed with nitrogen gas and/or a nitrogen containing gas compound and the carbon and/or a carbon containing gas compound to facilitate in the formation of the ZrNC coating. When Zr metal particles are used, the initial Zr coating layer on the outer surface of the orthopedic medical device can optionally be eliminated. In one non-limiting embodiment, the enhancement coating composition generally includes 40-95 wt. % Zr (and all values and ranges therebetween), 5-40 wt. % N (and all values and ranges therebetween), and 5-40 wt. % C (and all values and ranges therebetween), 0-2 wt. % O (and all values and ranges therebetween), 0-10 wt. % Re (and all values and ranges therebetween), and 0-20 wt. % Si (and all values and ranges therebetween). In another non-limiting embodiment, the enhancement coating composition generally includes 40-80 wt. % Zr, 5-25 wt. % N, and 5-25 wt. % C, 0-1 wt. % O, 0-8 wt. % Re, and 0-1 wt. % Si.

In accordance with another and/or alternative non-limiting aspect of the present disclosure, the material used to form the orthopedic medical device contains little or no nickel. Nickel and cobalt are commonly used in commercial orthopedic medical devices, even though such materials have exhibited suboptimal results in terms of biocompatibility. In one non-limiting embodiments, the metal alloy used to form the orthopedic medical device includes only trace amounts (e.g., less than 0.1 wt. %) of cobalt and/or nickel. In another non-limiting configuration, the metal alloy used to form the orthopedic medical device is completely absent nickel and/or cobalt. In another non-limiting configuration, the metal alloy used to form the orthopedic medical device includes rhenium and optionally chromium and/or molybdenum. In another non-limiting configuration, the metal alloy used to form the orthopedic medical device includes up to 70 wt. % rhenium and one or more metals selected from the group consisting of Mo, Cr, Co, Ni, Ti, Ta, Nb, Zr, and/or W.

In accordance with another and/or alternative non-limiting aspect of the present disclosure, the material used to form the orthopedic medical device has high yield strength. In one non-limiting embodiment, the material used to form the orthopedic medical device has a yield strength of at least 110 ksi. In one non-limiting embodiment, the material used to form the orthopedic medical device has an elongation of at least 20%. In one non-limiting embodiment, the material used to form the orthopedic medical device has a yield strength of at least 110 Ksi and an elongation of at least 20%. In one non-limiting embodiment, the material used to form the orthopedic medical device has a yield strength of at least 110 Ksi and and/or an elongation of at least 20% when the expandable frame is in its finished state (e.g., Finished state is defined as material properties after undergoing any material processing such as heating, annealing, cold working, during manufacturing, hot working, etc. Finished state implies the material ready to be sterilized or implanted or shipped to customer in the form of a medical device).

In accordance with another and/or alternative non-limiting aspect of the present disclosure, the orthopedic medical device can optionally be fabricated from a material having no or substantially no shape-memory characteristics.

In accordance with another and/or alternative non-limiting aspect of the present disclosure, the orthopedic medical device can optionally be fabricated from a material having shape-memory characteristics.

In accordance with another and/or alternative non-limiting aspect of the present disclosure, the optional use of a metal alloy to partially or fully form the orthopedic medical device wherein the metal alloy includes at least 15 awt. % rhenium can be used to increase the strength and/or hardness and/or durability of the frame of the orthopedic medical device as compared with stainless steel or chromium-cobalt alloys or titanium alloys; thus, less quantity of metal alloy that includes at least 15 awt. % rhenium can be used in the frame of the orthopedic medical device to achieve similar strengths as compared to orthopedic medical devices formed of different metals. As such, the resulting orthopedic medical device can be made smaller and less bulky by use of the metal alloy that includes at least 5 awt. % (e.g., 5-99 awt. %) without sacrificing the strength and durability of the orthopedic medical device. Due to the improved physical properties of the orthopedic medical device from the metal alloy that includes at least 15 awt. % rhenium, the orthopedic medical device has improved resistance to fracturing in such frequent bending environments. In addition or alternatively, the improved bendability and flexibility of the orthopedic medical device due to the use of the metal alloy that includes at least 15 awt. % rhenium can enable the orthopedic medical device to be more easily inserted into various regions of a body. In addition to the improved physical properties of the orthopedic medical device by use of the metal alloy that includes at least 15 awt. % rhenium, the metal alloy that includes at least 15 awt. % rhenium can optionally have improved radiopaque properties as compared to standard materials such as stainless steel or cobalt-chromium alloy, thus reducing or eliminating the need for using marker materials on the orthopedic medical device.

In accordance with another and/or alternative non-limiting aspect of the present disclosure, the optional use of the metal alloy that includes at least 15 awt. % rhenium to form all or a portion of the orthopedic medical device can result in one or more advantages over orthopedic medical devices formed from other materials. These one or more advantages include, but are not limited to:

The metal alloy that includes at least 15 awt. % rhenium used to partially or fully form the frame of the orthopedic medical device optionally has increased strength and/or hardness as compared with stainless steel, chromium-cobalt alloys, or titanium alloys, thus a less quantity of metal alloy can be used in the orthopedic medical device to achieve similar strengths as compared to orthopedic medical devices formed of different metals.

The metal alloy that includes at least 15 awt. % rhenium used to partially or fully form the frame of the orthopedic medical device optionally has improved radiopaque properties compared to standard materials such as stainless steel or cobalt-chromium alloy, thus reducing or eliminating the need for using marker materials on the orthopedic medical device. For example, the metal alloy is at least about 10-20% more radiopaque than stainless steel or cobalt-chromium alloy.

The metal alloy that includes at least 15 awt. % rhenium used to partially or fully form the frame of the orthopedic medical device optionally has improved fatigue ductility when subjected to cold-working compared to the cold-working of stainless steel, chromium-cobalt alloys, or titanium alloys.

The metal alloy that includes at least 15 awt. % rhenium used to partially or fully form the frame of the orthopedic medical device optionally has improved durability compared to stainless steel, chromium-cobalt alloys, or titanium alloys.

The metal alloy that includes at least 15 awt. % rhenium used to partially or fully form the frame of the orthopedic medical device optionally has improved hydrophilicity compared to stainless steel, chromium-cobalt alloys, or titanium alloys.

The metal alloy that includes at least 15 awt. % rhenium used to partially or fully form the orthopedic medical device can have improved durability as compared to similar sized and shaped orthopedic medical devices that are formed of stainless steel, chromium-cobalt alloys, or titanium alloys.

The metal alloy that includes at least 15 awt. % rhenium used to partially or fully form the orthopedic medical device can have improved hydrophilicity as compared to similar sized and shaped orthopedic medical devices that are formed of stainless steel, chromium-cobalt alloys, or titanium alloys.

The metal alloy that includes at least 15 awt. % rhenium used to partially or fully form the orthopedic medical device can have reduced ion release in the body as compared to similar sized and shaped orthopedic medical devices that are formed of stainless steel, chromium-cobalt alloys, or titanium alloys.

The metal alloy that includes at least 15 awt. % rhenium used to partially or fully form the orthopedic medical device is fully absent nickel and/or chromium content or has reduced amounts of nickel and/or chromium as compared to orthopedic medical devices that are partially or fully formed of stainless steel alloy, cobalt-chromium alloy, and TiNi alloy so as to reduce or eliminate problems associated with allergic reactions with surrounding tissue that can be at least partially caused by chromium and/or nickel.

The metal alloy that includes at least 15 awt. % rhenium used to partially or fully form the orthopedic medical device has reduced ion release of nickel and/or chromium so as to reduce or eliminate problems associated with allergic reactions with surrounding tissue that can be at least partially caused by chromium and/or nickel.

The metal alloy that includes at least 15 awt. % rhenium used to partially or fully form the orthopedic medical device can be less of an irritant to the cells about the implanted orthopedic medical device as compared to similar sized and shaped orthopedic medical devices that are formed of stainless steel, chromium-cobalt alloys, or titanium alloys.

The metal alloy that includes at least 15 awt. % rhenium used to partially or fully form the frame of the orthopedic medical device optionally has reduced ion release in the body passageway compared to stainless steel, chromium-cobalt alloys, or titanium alloys.

The metal alloy that includes at least 15 awt. % rhenium used to partially or fully form the frame of the orthopedic medical device optionally is less of an irritant to the body than stainless steel, cobalt-chromium alloy, or titanium alloys, thus can result in reduced inflammation, faster healing, increased success rates of the orthopedic medical device. When one or more portions of the orthopedic medical device includes an enhancement coating (e.g., TiNOx, ZrNxOy, etc.), such coating can be used to optionally further reduce irritation to the cells about the orthopedic medical device and/or facilitate in the generation of nitric oxide on the surface of the coating, and thus improve healing and/or operational longevity of the orthopedic medical device.

An orthopedic medical device that include an includes an enhancement coating can a) reduce or eliminate problems associated with allergic reactions with surrounding tissue that can be at least partially caused by chromium and/or nickel, b) increases the surface hardness of the orthopedic medical device, c) promotes the formation and/or release of nitric oxide (NO) from the implanted orthopedic medical device so as to improve the success rate of the implanted orthopedic medical device, d) promotes bone healing about the implanted orthopedic medical device, e) reduces bacterial growth and/or bacterial infection about the implanted orthopedic medical device, and/or f) has an outer surface that improves the biocompatibility of the implanted orthopedic medical device.

The metal alloy that includes at least 15 awt. % rhenium used to partially or fully form the frame of the orthopedic medical device optionally has a magnetic susceptibility that is lower than similar sized and shaped orthopedic medical devices that are formed of stainless steel, chromium-cobalt alloys, or titanium alloys, thus resulting in less incidence of potential defects to the orthopedic medical device or complications to the patent after implantation of the orthopedic medical device when the patient is subjected to an MRI or other orthopedic medical device that generates a strong magnetic field.

One non-limiting object of the present disclosure is the provision of an orthopedic medical device wherein a portion or all of the outer surface is coated with an enhancement coating.

Another and/or alternative non-limiting object of the present disclosure is the provision of an orthopedic medical device wherein a portion or all of the outer surface is coated with an enhancement coating that includes TiNOx and/or ZrNxOy so as to a) promote the formation and/or release of nitric oxide (NO) from the implanted orthopedic medical device so as to improve the success rate of the implanted orthopedic medical device, b) promotes bone healing about the implanted orthopedic medical device, c) reduces bacterial growth and/or bacterial infection about the implanted orthopedic medical device, and/or d) has an outer surface that improves the biocompatibility of the implanted orthopedic medical device.

Another and/or alternative non-limiting object of the present disclosure is the provision of an orthopedic medical device wherein a portion or all of the orthopedic medical device includes a refractory metal alloy or a metal alloy that includes at least 5 awt. % (e.g., 5-99 awt. % and all values and ranges therebetween) rhenium.

Another and/or alternative non-limiting object of the present disclosure is the provision of an orthopedic medical device that is coated with an enhancement coating that facilitates in the formation of nitric oxide (NO) production.

Another and/or alternative non-limiting object of the present disclosure is the provision of an orthopedic medical device that includes a metal selected from the group consisting of a) stainless steel, b) cobalt-chromium alloy, c) titanium-aluminum-vanadium alloy, d) aluminum alloy, e) nickel alloy, f) titanium alloy, g) tungsten alloy, h) molybdenum alloy, i) copper alloy, j) beryllium-copper alloy, k) titanium-nickel alloy, l) refractory metal alloy, or m) metal alloy that includes at least metal alloy that includes at least 5 atomic weight percent (awt. %) or atomic percent (awt %) rhenium (e.g., 5-99 awt. % rhenium and all values and ranges therebetween); the enhancement material is formulated to provide nitric oxide or its precursors nitrogen and oxygen, ii) promote generation of nitric oxide in adjacent tissue, and/or iii) promote transport of nitric oxide to adjacent tissue.

Another and/or alternative non-limiting object of the present disclosure is the provision of an orthopedic medical device that has one or more of the following properties: i) at least 70-100% of the orthopedic medical device is formed of a metal alloy that has a yield strength of at least 110 ksi, ii) at least 70-100% of the orthopedic medical device is formed of a metal alloy that has a modulus of elasticity of at least 35000 ksi, iii) at least 70-100% of the orthopedic medical device is formed of a metal alloy that is formed of a rhenium containing metal alloy that includes at least 0.1 wt. % rhenium and one or more metals selected from the group consisting of Mo, Cr, Co, Ni, Ti, Ta, Nb, Zr, and W.

Another and/or alternative non-limiting object of the present disclosure is the provision of an orthopedic medical device wherein the enhancement coating includes an outer metal oxynitride layer.

Another and/or alternative non-limiting object of the present disclosure is the provision of an orthopedic medical device wherein the enhancement coating (e.g., outer metal oxynitride layer, etc.) includes titanium oxynitride and/or zirconium oxynitride.

Another and/or alternative non-limiting object of the present disclosure is the provision of an orthopedic medical device wherein the enhancement coating (e.g., outer metal oxynitride layer, etc.) optionally has a thickness of 10 nanometers (e.g., 10 nanometers to 10 microns and all values and ranges therebetween).

Another and/or alternative non-limiting object of the present disclosure is the provision of an orthopedic medical device wherein the enhancement coating (e.g., outer metal oxynitride layer, etc.) optionally has an oxygen to nitrogen atomic ratio of 1:10 to 10:1.

Another and/or alternative non-limiting object of the present disclosure is the provision of an orthopedic medical device wherein the enhancement coating optionally includes no more than 0.1 wt. % nickel and/or no more than 0.1 wt. % cobalt; the orthopedic device is optionally a) a spinal implant, b) a frame and other structure for use with a spinal implant, c) a bone implant, d) an artificial disk, e) an artificial spinal disk, f) a spinal interbody, g) an expandable spinal interbody, h) an interbody fusion device, i) an expandable interbody fusion device, j) a prosthetic implant or device to repair, replace and/or support a bone and/or cartilage, k) a bone plate nail, l) a spinal rod, m) a bone screw, n) a post, o) a spinal cage, p) a bone plate, q) a pedicle screw, r) a cap, s) a hinge, t) a joint system, u) an anchor, v) a spacer, w) a shaft, x) an anchor, y) a disk, z) a ball, aa) a tension band, or ab) a locking connector or other structural assembly that is used in a body to support a structure, mount a structure, and/or repair a structure in a body.

Another and/or alternative non-limiting object of the present disclosure is the provision of an orthopedic medical device wherein the enhancement coating includes an outer metal oxynitride layer and a metallic adhesion layer; the outer metal oxynitride layer is optionally coated on an outer surface of the metallic adhesion layer, or the metallic adhesion layer is optionally coated on an outer surface of the orthopedic medical device; the metallic adhesion layer optionally includes titanium metal or zirconium metal; the metallic adhesion layer optionally has a thickness of 1 to 500 nanometers. The enhancement coating and/or the metallic adhesion layer can be applied by use of a vacuum coating process (e.g., physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process), plating process, etc.

Another and/or alternative non-limiting object of the present disclosure is the provision of an orthopedic medical device wherein the orthopedic medical device includes no more than 0.1 wt. % nickel and/or no more than 0.1 wt. % cobalt.

Another and/or alternative non-limiting object of the present disclosure is the provision of an orthopedic medical device wherein the orthopedic medical device is formed of the refractory metal alloy or the metal alloy that includes at least metal alloy that includes at least 5 atomic weight percent (awt. %) or atomic percent (awt %) rhenium (e.g., 5-99 awt. % rhenium and all values and ranges therebetween).

Another and/or alternative non-limiting object of the present disclosure is the provision of an orthopedic medical device wherein the orthopedic medical device is formed of at least 0.1 wt. % rhenium and one or more metal selected from molybdenum, chromium, cobalt, nickel, titanium, tantalum, niobium, zirconium, and/or tungsten.

Another and/or alternative non-limiting object of the present disclosure is the provision of an orthopedic medical device that includes no more than 0.1 wt. % nickel and/or no more than 0.1 wt. % cobalt.

Another and/or alternative non-limiting object of the present disclosure is the provision of an orthopedic medical device that is formed of a base material and an enhancement coating; the medical device is at least partially formed from a metal selected from a metal selected from the group consisting of a) stainless steel, b) cobalt-chromium alloy, c) titanium-aluminum-vanadium alloy, d) aluminum alloy, e) nickel alloy, f) titanium alloy, g) tungsten alloy, h) molybdenum alloy, i) copper alloy, j) beryllium-copper alloy, k) titanium-nickel alloy, l) refractory metal alloy, or m) metal alloy that includes at least metal alloy that includes at least 5 atomic weight percent (awt. %) or atomic percent (awt %) rhenium (e.g., 5-99 awt. % rhenium and all values and ranges therebetween); and wherein the enhancement coating is coated on an outer surface of at least a portion of the orthopedic medical device.

Another and/or alternative non-limiting object of the present disclosure is the provision of an orthopedic medical device wherein at least a portion of the orthopedic medical device includes an enhancement coating that promotes nitric oxide generation, and wherein the nitric oxide donation includes use of a nitric oxide donating compound; the nitric oxide donating compound is a) a direct nitric oxide donator, wherein the direct nitric oxide donator includes S—NO—N-acetyl-L-cysteine, Molsidomine, Diethylamino-NONOate, Spermine NONOate, S—NO-Glutathione, and/or S—NO-diclofenac, b) a metabolic nitric oxide donator, wherein the metabolic nitric oxide donator includes nitroglycerin, amyl nitrite, isosorbide dinitrate, isosorbide mononitrate, and/or nicorandil, and/or c) a bifunctional nitric oxide donator, wherein the bifunctional nitric oxide donator includes nitroaspirins and/or S-Nitroso-NTHEs.

Another and/or alternative non-limiting object of the present disclosure is the provision of an orthopedic medical device that includes an enhancement material that is at least partially coated on the orthopedic medical device, and wherein the enhancement material is formulated to i) provide nitric oxide, and/or ii) promote generation of nitric oxide; the enhancement material is at least partially formulated of oxynitride, and wherein the enhancement material optionally includes metal oxynitride, and wherein the metal oxynitride optionally includes titanium oxynitride and/or zirconium oxynitride, and wherein the enhancement coating optionally has a thickness of at least 1 nanometers (e.g., 1 nanometers to 10 microns and all values and ranges therebetween), and wherein the metal oxynitride optionally has an oxygen to nitrogen atomic ratio of 1:10 to 10:1 (and all values and ranges therebetween), and wherein the enhancement coating is optionally at least partially coated on a metallic adhesion layer; and wherein the oxynitride is optionally at least partially coated on an outer surface of the metallic adhesion layer or the metallic adhesion layer that is optionally at least partially coated on an outer surface of the orthopedic medical device, and wherein the metallic adhesion layer optionally includes titanium metal or zirconium metal, and wherein the enhancement coating optionally includes no more than 0.1 wt. % nickel and/or no more than 0.1 wt. % cobalt and/or no more than 0.1 wt. % chromium, and wherein the metallic adhesion layer optionally includes no more than 0.1 wt. % nickel, no more than 0.1 wt. % chromium and/or no more than 0.1 wt. % cobalt, and wherein the metal used to form the orthopedic medical device optionally includes no more than 0.1 wt. % nickel, no more than 0.1 wt. % chromium and/or no more than 0.1 wt. % cobalt, and wherein the metal used to form the orthopedic medical device is optionally formed of a) stainless steel, b) cobalt-chromium alloy, c) titanium-aluminum-vanadium alloy, d) aluminum alloy, e) nickel alloy, f) titanium alloy, g) tungsten alloy, h) molybdenum alloy, i) copper alloy, j) beryllium-copper alloy, k) titanium-nickel alloy, l) refractory metal alloy, or m) metal alloy that includes at least 5 atomic weight percent (awt. %) rhenium (e.g., 5-99 awt. % rhenium and all values and ranges therebetween), and wherein the orthopedic medical device is optionally formed of at least 0.1 wt. % rhenium and one or more metal selected from molybdenum, chromium, cobalt, nickel, titanium, tantalum, niobium, zirconium, and/or tungsten, and wherein the orthopedic device is optionally a) a spinal implant, b) a frame and other structure for use with a spinal implant, c) a bone implant, d) an artificial disk, e) an artificial spinal disk, f) a spinal interbody, g) an expandable spinal interbody, h) an interbody fusion device, i) an expandable interbody fusion device, j) a prosthetic implant or device to repair, replace and/or support a bone and/or cartilage, k) a bone plate nail, l) a spinal rod, m) a bone screw, n) a post, o) a spinal cage, p) a bone plate, q) a pedicle screw, r) a cap, s) a hinge, t) a joint system, u) an anchor, v) a spacer, w) a shaft, x) an anchor, y) a disk, z) a ball, aa) a tension band, or ab) a locking connector or other structural assembly that is used in a body to support a structure, mount a structure, and/or repair a structure in a body.

These and other advantages will become apparent to those skilled in the art upon the reading and following of this description and along with the figures.

BRIEF DESCRIPTION OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. Reference may now be made to the drawings, which illustrate various embodiments that the disclosure may take in physical form and in certain parts and arrangement of parts wherein:

FIG. 1 is a cross-sectional view of a section of a portion of an orthopedic medical device that illustrates an enhancement coating on the outer surface of a section of the base material of the orthopedic medical device.

FIG. 2 is a cross-sectional view of a section of a portion of an orthopedic medical device that illustrates an enhancement coating on the outer surface of a pre-applied metal layer that is coated on the outer surface of a section of the base material of the orthopedic medical device.

DESCRIPTION OF NON-LIMITING EMBODIMENTS OF THE DISCLOSURE

A more complete understanding of the articles/devices, processes and components disclosed herein can be obtained by reference to the accompanying drawings. These figures are merely schematic representations based on convenience and the case of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

The singular forms "a," "an," and "the" include plural referents unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated ingredients/steps, which allows the presence of only the named ingredients/steps, along with any unavoidable impurities that might result therefrom, and excludes other ingredients/steps.

Numerical values in the specification and claims of this application should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The terms "about" and "approximately" can be used to include any numerical value that can vary without changing the basic function of that value. When used with a range, "about" and "approximately" also disclose the range defined by the absolute values of the two endpoints, e.g., "about 2 to about 4" also discloses the range "from 2 to 4." Generally, the terms "about" and "approximately" may refer to plus or minus 10% of the indicated number.

Percentages of elements should be assumed to be percent by weight of the stated element, unless expressly stated otherwise.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

For the sake of simplicity, the attached figures may not show the various ways (readily discernable, based on this disclosure, by one of ordinary skill in the art) in which the disclosed system, method and apparatus can be used in combination with other systems, methods and apparatuses. Additionally, the description sometimes uses terms such as "produce" and "provide" to describe the disclosed method. These terms are abstractions of the actual operations that can be performed. The actual operations that correspond to these terms can vary depending on the particular implementation and are, based on this disclosure, readily discernible by one of ordinary skill in the art.

Referring now to FIG. 1, the present disclosure is directed to an orthopedic medical device OMD that includes an enhancement coating 102. The type of orthopedic medical device OMD is non-limiting. Such orthopedic medical devices OMD can include, but are not limited to, a spinal implant, frame and other structure for use with a spinal implant, bone implant, artificial disk, artificial spinal disk, spinal interbody, expandable spinal interbody, interbody fusion device, expandable interbody fusion device, prosthetic implant or device to repair, replace and/or support a bone (e.g., acromion, atlas, axis, calcaneus, carpus, clavicle, coccyx, epicondyle, epitrochlea, femur, fibula, frontal bone, greater trochanter, humerus, ilium, ischium, mandible, maxilla, metacarpus, metatarsus, occipital bone, olecranon, parietal bone, patella, phalanx, radius, ribs, sacrum, scapula, sternum, talus, tarsus, temporal bone, tibia, ulna, zygomatic bone, etc.) and/or cartilage, bone plate nail, spinal rod, bone screw, post, spinal cage, bone plate, pedicle screw, cap, hinge, joint system, anchor, spacer, shaft, anchor, disk, ball, tension band, locking connector or other structural assembly that is used in a body to support a structure, mount a structure, and/or repair a structure in a body such as, but not limited to, a human body, animal body, etc.

FIG. 1 illustrates an enlarged cross-sectional portion of an orthopedic medical device OMD. The orthopedic medical device OMD is formed of a base material 100 and the enhancement coating 102 can be applied directed to the outer surface 104 of the base material 100.

The base material can be formed of a variety of materials (e.g., polymer, metal, composite material, ceramic, etc.). In one non-limiting configuration, the base material 102 is formed of a metal material. Such metal material can partially or fully constitute the base material 102 of the orthopedic medical device OMD. Non-limiting metal material that can be used to form the orthopedic medical device includes a) stainless steel, b) CoCr alloy or MP35N alloy or a Phynox alloy or Elgiloy alloy or L605 alloy, c) TiAlV alloy, d) aluminum alloy, e) nickel alloy, f) titanium alloy, g) tungsten alloy, h) molybdenum alloy, i) copper alloy, j) beryllium-copper alloy, k) Nitinol alloy, l) refractory metal alloy, or m) metal alloy that includes at least metal alloy that includes at least 5 atomic weight percent (awt. %) or atomic percent (awt %) rhenium (e.g., 5-99 awt. % rhenium and all values and ranges therebetween). In one non-limiting configuration, 10-100 wt. % of the orthopedic medical device includes refractory metal alloy, or a metal alloy that includes at least 15 atomic weight percent (awt. %) rhenium. In one non-limiting configuration, the metal material includes at least 0.1 wt. % (e.g., 0.1-70 wt. % and all values and ranges therebetween) rhenium and one or more metals selected from the group of molybdenum, chromium, cobalt, nickel, titanium, tantalum, niobium, zirconium, and/or tungsten. In one non-limiting configuration, the metal material includes at least 5 wt. % (e.g., 5-70 wt. % and all values and ranges therebetween) rhenium and one or more metals selected from the group of molybdenum, chromium, cobalt, nickel, titanium, tantalum, niobium, zirconium, and/or tungsten.

Non-limiting enhancement coatings 102 that can be applied to a portion or all of the outer surface 104 of the base material 100 of the orthopedic medical device includes chromium nitride (CrN), diamond-like carbon (DLC), titanium nitride (TiN), titanium oxynitride or titanium nitride oxide (TiNOx), zirconium nitride (ZrN), zirconium oxide ($ZrO_2$), zirconium oxynitride (ZrNxOy) [e.g., cubic ZrN:O, cubic $ZrO_2$:N, tetragonal $ZrO_2$:N, and monoclinic $ZrO_2$:N phase coatings], oxyzirconium-nitrogen-carbon (ZrNC), zirconium OxyCarbide (ZrOC), and combinations of such coatings. The process used to apply the enhancement coating can include physical vapor deposition (PVD) process (e.g., sputter deposition, cathodic arc deposition or electron beam heating, etc.), chemical vapor deposition (CVD) process, atomic layer deposition (ALD) process, or a plasma-enhanced chemical vapor deposition (PE-CVD) process. The thickness of the enhancement coating 102 is greater than 1 nanometer (e.g., 2 nanometers to 100 microns and all values and ranges therebetween).

Referring now to FIG. 2, the enhancement coating 102 can alternatively be coated on a metal coating layer 106 (e.g., titanium layer, zirconium layer, etc.), which is in turn coated on to the outer surface 104 of the base material 100. The type of metal material used on the optional metal coating layer 106 is non-limiting. The thickness of the metal coating layer 106 is generally at least 0.05 microns, and typically 0.05-15 microns. The coating process to apply the metal coating layer 106 on the outer surface is non-limiting (e.g., PVD, CVD, ALD, PE-CVD in an inert environment, etc.).

The enhancement coating 102 can be used to improve one or more properties of the orthopedic medical device (e.g., change exterior color of material having coated surface, increase surface hardness by use of the coated surface, increase surface toughness material having coated surface, reduced friction via use of the coated surface, improve scratch resistance of material that has the coated surface, improve impact wear of coated surface, improve resistance to corrosion and oxidation of coated material, form a non-stick coated surface, improve biocompatibility of material having the coated surface, reduce toxicity of material having the coated surface, reduce ion release from material having the coated surface, the enhancement coating forms a surface that is less of an irritant to cell about the coated surface after the orthopedic medical device is implanted, facilitate in nitric oxide generation on the surface of the coating, reduce rate of bacterial growth on the outer surface of the orthopedic medical device, reduce infection rates, etc.).

Non-limiting enhancement coatings that can be applied to a portion or all of the outer surface of the orthopedic medical device includes chromium nitride (CrN), diamond-like carbon (DLC), titanium nitride (TiN), titanium oxynitride or titanium nitride oxide (TiNOx), zirconium nitride (ZrN), zirconium oxide ($ZrO_2$), zirconium-nitrogen-carbon (ZrNC), zirconium OxyCarbide (ZrOC), zirconium oxynitride ($ZrN_xO_y$), and combinations of such coatings. In one one-limiting configuration, a portion or all of the outer surface of the orthopedic medical device includes titanium oxynitride or titanium nitride oxide (TiNOx) and/or zirconium oxynitride ($ZrN_xO_y$). The enhancement coating can optionally be applied to a portion or all of the outer surface of the orthopedic medical device.

In one non-limiting embodiment, when forming a titanium oxynitride or titanium nitride oxide (TiNOx) coating on the orthopedic medical device, the portion of the orthopedic medical device that is to be coated can be optionally initially coated with Ti metal. The Ti metal coating, when applied, can be applied by PVD, CVD, ALD and PE-CVD in an inert environment. The coating thickness of Ti metal is 0.05-1 microns. Thereafter, the Ti metal coating is exposed to a nitrogen and oxygen mixture that can include nitrogen gas, oxygen gas, a nitrogen containing gas compound and/or an oxygen containing gas compound to cause the nitrogen and oxygen to react with the Ti metal coating. During the formation of the titanium oxynitride or titanium nitride oxide (TiNOx) coating, titanium particles can also be applied to the outer surface of the Ti metal coating prior to and/or during the exposure of the Ti metal coating to the nitrogen and oxygen mixture. The ratio of the N to the O can be varied to control the amount of O in the TiNOx coating. The ratio of N to O when forming the TiNOx coating is generally 1:10 to 10:1 (and all values and ranges therebetween). The coating thickness of the TiNOx coating is generally 0.1-2 microns (and all values and ranges therebetween).

In another non-limiting embodiment, when forming a titanium oxynitride or titanium nitride oxide (TiNOx) coating on the orthopedic medical device, the portion of the orthopedic medical device that is to be coated is exposed to titanium particles and a nitrogen and oxygen mixture that can include nitrogen gas, oxygen gas, a nitrogen containing gas compound and/or an oxygen containing gas compound to cause the nitrogen and oxygen to react with the Ti particles. In this coating method, a Ti coating is not preapplied to the outer surface of any portion of the orthopedic medical device that is to be coated with titanium oxynitride or titanium nitride oxide (TiNOx). The ratio of the N to the O can be varied to control the amount of O in the TiNOx coating. The ratio of N to O when forming the TiNOx coating is generally 1:10 to 10:1 (and all values and ranges therebetween). The coating thickness of the TiNOx coating is generally 0.1-2 microns (and all values and ranges therebetween).

In one non-limiting embodiment, when forming a zirconium oxynitride ($ZrN_xO_y$) coating on the orthopedic medical device, the portion of the orthopedic medical device that is to be coated can be optionally initially coated with Zr metal. The Zr metal coating, when applied, can be applied by PVD, CVD, ALD and PE-CVD in an inert environment. The coating thickness of Zr metal is 0.05-1 microns. Thereafter, the Zr metal coating is exposed to a nitrogen and oxygen mixture that can include nitrogen gas, oxygen gas, a nitrogen containing gas compound and/or an oxygen containing gas compound to cause the nitrogen and oxygen to react with the Zr metal coating. During the formation of the zirconium oxynitride ($ZrN_xO_y$) coating, zirconium particles can also be applied to the outer surface of the Zr metal coating prior to and/or during the exposure of the Zr metal coating to the nitrogen and oxygen mixture. The ratio of the N to the O can be varied to control the amount of O in the $ZrN_xO_y$ coating. The ratio of N to O when forming the $ZrN_xO_y$ coating is generally 1:10 to 10:1 (and all values and ranges therebetween). The coating thickness of the $ZrN_xO_y$ coating is generally 0.1-2 microns (and all values and ranges therebetween).

In another non-limiting embodiment, when forming a zirconium oxynitride ($ZrN_xO_y$) coating on the orthopedic medical device, the portion of the orthopedic medical device that is to be coated is exposed to zirconium particles and a nitrogen and oxygen mixture that can include nitrogen gas, oxygen gas, a nitrogen containing gas compound and/or an oxygen containing gas compound to cause the nitrogen and oxygen to react with the Zr particles. In this coating method, a Zr coating is not preapplied to the outer surface of any portion of the orthopedic medical device that is to be coated with zirconium oxynitride ($ZrN_xO_y$) coating. The ratio of the N to the O can be varied to control the amount of O in the $ZrN_xO_y$ coating. The ratio of N to O when forming the $ZrN_xO_y$ coating is generally 1:10 to 10:1 (and all values and ranges therebetween). The coating thickness of the $ZrN_xO_y$ coating is generally 0.1-2 microns (and all values and ranges therebetween).

It will thus be seen that the objects set forth above, among those made apparent from the preceding description, are efficiently attained, and since certain changes may be made in the constructions set forth without departing from the spirit and scope of the disclosure, it is intended that all matter contained in the above description and shown in the accompanying drawings shall be interpreted as illustrative and not in a limiting sense. The disclosure has been described with reference to preferred and alternate embodiments. Modifications and alterations will become apparent to those skilled in the art upon reading and understanding the detailed discussion of the disclosure provided herein. This disclosure is intended to include all such modifications and alterations insofar as they come within the scope of the present disclosure. It is also to be understood that the following claims are intended to cover all of the generic and specific features of the disclosure herein described and all statements of the scope of the disclosure, which, as a matter of language, might be said to fall therebetween.

To aid the Patent Office and any readers of this application and any resulting patent in interpreting the claims appended hereto, applicants do not intend any of the appended claims or claim elements to invoke 35 U.S.C. 112(f) unless the words "means for" or "step for" are explicitly used in the particular claim.

What is claimed:

1. An orthopedic medical device that is formed of a base material and an enhancement coating; said orthopedic medical device is at least partially formed from a metal alloy that is selected from the group consisting of a) stainless steel, b) cobalt-chromium alloy, c) titanium-aluminum-vanadium alloy, d) aluminum alloy, e) nickel alloy, f) titanium alloy, g) tungsten alloy, h) molybdenum alloy, i) copper alloy, j) beryllium-copper alloy, k) titanium-nickel alloy, l) refractory metal alloy, or m) metal alloy that includes at least 5 atomic weight percent (awt. %) rhenium; said enhancement coating is formulated to promote generation of nitric oxide on an outer surface of said enhancement coating; said enhancement coating is directly coated on at least a portion of an outer surface of said base material that is formed of said metal alloy; a thickness of said coating material is less than a thickness of said base material; said enhancement coating is formed of a) a coating material that is titanium oxynitride and/or zirconium oxynitride that is coated on said outer surface of base material that is formed of said metal alloy of said base material, or b) a metallic adhesion layer and a coating material, and wherein said coating material is titanium oxynitride and/or zirconium oxynitride, and wherein said metallic adhesion layer is a layer of metal that is coated on an outer surface of said base material and said coating material is coated on an outer surface of said metallic adhesion layer, and wherein said metallic adhesion layer is titanium, titanium alloy, zirconium or zirconium alloy.

2. The orthopedic medical device as defined in claim 1, wherein said coating material is titanium oxynitride or zirconium oxynitride.

3. The orthopedic medical device as defined in claim 1, wherein coating material has a thickness of 10 nanometers to 10 microns.

4. The orthopedic medical device as defined in claim 2, wherein said material oxynitride has a thickness of 10 nanometers to 10 microns.

5. The orthopedic medical device as defined in claim 1, wherein said coating material has an oxygen to nitrogen atomic ratio of 1:10 to 10:1.

6. The orthopedic medical device as defined in claim 2, wherein said coating material has an oxygen to nitrogen atomic ratio of 1:10 to 10:1.

7. The orthopedic medical device as defined in claim 1, wherein said enhancement coating includes said coating material and said metallic adhesion layer.

8. The orthopedic medical device as defined in claim 2, wherein said enhancement coating includes said coating material and said metallic adhesion layer.

9. The orthopedic medical device as defined in claim 7, wherein said metallic adhesion layer includes titanium metal or zirconium metal.

10. The orthopedic medical device as defined in claim 8, wherein said metallic adhesion layer includes titanium metal or zirconium metal.

11. The orthopedic medical device as defined in claim 7, wherein said metallic adhesion layer has a thickness of 1 to 500 nanometers.

12. The orthopedic medical device as defined in claim 8, wherein said metallic adhesion layer has a thickness of 1 to 500 nanometers.

13. The orthopedic medical device as defined in claim 1, wherein said enhancement coating includes no more than 0.1 wt. % nickel, no more than 0.1 wt. % chromium, and/or no more than 0.1 wt. % cobalt.

14. The orthopedic medical device as defined in claim 2, wherein said enhancement coating includes no more than 0.1 wt. % nickel, no more than 0.1 wt. % chromium, and/or no more than 0.1 wt. % cobalt.

15. The orthopedic medical device as defined in claim 1, wherein said base material includes no more than 0.1 wt. % nickel, no more than 0.1 wt. % chromium, and/or no more than 0.1 wt. % cobalt.

16. The orthopedic medical device as defined in claim 2, wherein said base material includes no more than 0.1 wt. % nickel, no more than 0.1 wt. % chromium, and/or no more than 0.1 wt. % cobalt.

17. The orthopedic medical device as defined in claim 1, wherein said base material is formed of said refractory metal alloy or said metal alloy that includes at least 15 atomic weight percent (awt. %) rhenium.

18. The orthopedic medical device as defined in claim 2, wherein said base material is formed of said refractory metal alloy or said metal alloy that includes at least 15 atomic weight percent (awt. %) rhenium.

19. The orthopedic medical device as defined in claim 1, wherein said base material is formed of at least 0.1 wt. % rhenium and one or more metal selected from molybdenum, chromium, cobalt, nickel, titanium, tantalum, niobium, zirconium, and/or tungsten.

20. The orthopedic medical device as defined in claim 2, wherein said base material is formed of at least 0.1 wt. % rhenium and one or more metal selected from molybdenum, chromium, cobalt, nickel, titanium, tantalum, niobium, zirconium, and/or tungsten.

21. The orthopedic medical device as defined in claim 1, wherein said orthopedic medical device is a) a spinal implant, b) a frame for use with a spinal implant, c) a bone implant, d) an artificial disk, e) an artificial spinal disk, f) a spinal interbody, g) an expandable spinal interbody, h) an interbody fusion device, i) an expandable interbody fusion device, j) a prosthetic implant to repair, replace and/or support a bone and/or cartilage, k) a bone plate nail, l) a spinal rod, m) a bone screw, n) a post, o) a spinal cage, p) a bone plate, q) a pedicle screw, r) a cap, s) a hinge, t) a joint system, u) an anchor, v) a spacer, w) a shaft, x) an anchor, y) a disk, z) a ball, aa) a tension band, or ab) a locking connector that is used in a body to support the structure, mount the structure, and/or repair the structure in a body.

22. The orthopedic medical device as defined in claim 2, wherein said orthopedic medical device is a) a spinal implant, b) a frame for use with a spinal implant, c) a bone implant, d) an artificial disk, e) an artificial spinal disk, f) a spinal interbody, g) an expandable spinal interbody, h) an interbody fusion device, i) an expandable interbody fusion device, j) a prosthetic implant to repair, replace and/or support a bone and/or cartilage, k) a bone plate nail, l) a spinal rod, m) a bone screw, n) a post, o) a spinal cage, p) a bone plate, q) a pedicle screw, r) a cap, s) a hinge, t) a joint system, u) an anchor, v) a spacer, w) a shaft, x) an anchor, y) a disk, z) a ball, aa) a tension band, or ab) a locking connector that is used in a body to support the structure, mount the structure, and/or repair the structure in a body.

23. An orthopedic medical device that is formed of a base material and an enhancement coating that is coated on at least a portion of an outer surface of said base material; said base material is formed of a metal alloy that is selected from the group consisting of a) stainless steel, b) cobalt-chromium alloy, c) titanium-aluminum-vanadium alloy, d) aluminum alloy, e) nickel alloy, f) titanium alloy, g) tungsten alloy, h) molybdenum alloy, i) copper alloy, j) beryllium-copper alloy, k) titanium-nickel alloy, l) refractory metal alloy, or m) metal alloy that includes at least 5 atomic weight percent (awt. %) rhenium; said enhancement coating is formulated to i) promote generation of nitric oxide in adjacent tissue, and/or ii) promote transport of nitric oxide to adjacent tissue; said enhancement coating is formed of a) a coating material that is titanium oxynitride that is coated on said outer surface of base material that is formed of said metal alloy of said base material, or b) a metallic adhesion layer and a coating material, and wherein said coating material is titanium oxynitride, and wherein said metallic adhesion layer is a layer of metal that is coated on an outer surface of said base material and said coating material is coated on an outer surface of said metallic adhesion layer, and wherein said metallic adhesion layer is titanium or titanium alloy; said coating material has a thickness of 10 nanometers to 10 microns; said coating material has an oxygen to nitrogen atomic ratio of 1:10 to 10:1; said coating material includes no more than 0.1 wt. % nickel, no more than 0.1 wt. % chromium, and/or no more than 0.1 wt. % cobalt; said orthopedic medical device is a) a spinal implant, b) a frame for use with a spinal implant, c) a bone implant, d) an artificial disk, e) an artificial spinal disk, f) a spinal interbody, g) an expandable spinal interbody, h) an interbody fusion device, i) an expandable interbody fusion device, j) a prosthetic implant to repair, replace and/or support a bone and/or cartilage, k) a bone plate nail, l) a spinal rod, m) a bone screw, n) a post, o) a spinal cage, p) a bone plate, q) a pedicle screw, r) a cap, s) a hinge, t) a joint system, u) an anchor, v) a spacer, w) a shaft, x) an anchor, y) a disk, z) a ball, aa) a tension band, or ab) a locking connector that is used in a body to support the structure, mount the structure, and/or repair the structure in a body; said thickness of said coating material is less than a thickness of said base material.

24. The orthopedic medical device as defined in claim 23, wherein said coating material is at least partially coated on said outer surface of said metallic adhesion layer; said metallic adhesion layer is titanium metal or zirconium metal; said metallic adhesion layer has a thickness of 1 to 500 nanometers.

25. The orthopedic medical device as defined in claim 23, wherein said base material includes no more than 0.1 wt. % nickel, no more than 0.1 wt. % chromium, and/or no more than 0.1 wt. % cobalt.

26. The orthopedic medical device as defined in claim 24, wherein said base material includes no more than 0.1 wt. % nickel, no more than 0.1 wt. % chromium, and/or no more than 0.1 wt. % cobalt.

27. The orthopedic medical device as defined in claim 23, wherein said base material is formed of said refractory metal alloy or said metal alloy that includes at least 15 atomic weight percent (awt. %) rhenium.

28. The orthopedic medical device as defined in claim 24, wherein said base material is formed of said refractory metal alloy or said metal alloy that includes at least 15 atomic weight percent (awt. %) rhenium.

29. The orthopedic medical device as defined in claim 23, wherein said base material is formed of at least 0.1 wt. % rhenium and one or more metal selected from molybdenum, chromium, cobalt, nickel, titanium, tantalum, niobium, zirconium, and/or tungsten.

30. The orthopedic medical device as defined in claim 24, wherein said base material is formed of at least 0.1 wt. % rhenium and one or more metal selected from molybdenum, chromium, cobalt, nickel, titanium, tantalum, niobium, zirconium, and/or tungsten.

* * * * *